(12) United States Patent
Shumaker-Parry et al.

(10) Patent No.: US 10,493,431 B2
(45) Date of Patent: Dec. 3, 2019

(54) NANODIAMOND SUPPORTED CATALYTIC NANOPARTICLES AND ASSOCIATED METHODS

(71) Applicant: University of Utah Research Foundation, Salt Lake City, UT (US)

(72) Inventors: Jennifer S. Shumaker-Parry, Salt Lake City, UT (US); Arthur D. Quast, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 58 days.

(21) Appl. No.: 15/691,505

(22) Filed: Aug. 30, 2017

(65) Prior Publication Data

US 2017/0361307 A1 Dec. 21, 2017

Related U.S. Application Data

(63) Continuation-in-part of application No. 15/625,725, filed on Jun. 16, 2017, now abandoned.

(60) Provisional application No. 62/351,177, filed on Jun. 16, 2016.

(51) Int. Cl.
| | |
|---|---|
| *B01J 21/18* | (2006.01) |
| *B01J 31/06* | (2006.01) |
| *B01J 23/52* | (2006.01) |
| *B01J 23/42* | (2006.01) |
| *B01J 23/44* | (2006.01) |
| *B01J 31/00* | (2006.01) |
| *B01J 35/00* | (2006.01) |
| *B01J 37/02* | (2006.01) |
| *B01J 37/04* | (2006.01) |
| *B01J 37/34* | (2006.01) |
| *G01N 31/10* | (2006.01) |
| *G01N 27/12* | (2006.01) |

(52) U.S. Cl.
CPC .............. *B01J 21/18* (2013.01); *B01J 23/42* (2013.01); *B01J 23/44* (2013.01); *B01J 23/52* (2013.01); *B01J 31/003* (2013.01); *B01J 31/06* (2013.01); *B01J 35/006* (2013.01); *B01J 35/0006* (2013.01); *B01J 35/0013* (2013.01); *B01J 37/0219* (2013.01); *B01J 37/04* (2013.01); *B01J 37/345* (2013.01); *G01N 31/10* (2013.01); *B01J 35/002* (2013.01); *B01J 37/0221* (2013.01); *B01J 37/0244* (2013.01); *B01J 2231/005* (2013.01); *B01J 2231/641* (2013.01); *B01J 2531/005* (2013.01); *G01N 27/127* (2013.01)

(58) Field of Classification Search
CPC ........ B01J 21/18; B01J 37/0221; B01J 23/44; B01J 23/52; B01J 37/345; B01J 37/04; B01J 37/0244; B01J 23/42; B01J 37/0219; B01J 35/0013; B01J 35/0006; B01J 31/06; B01J 31/003; B01J 2231/005; B01J 2231/641; B01J 2531/005; G01N 31/10

USPC ........................................................ 524/496
See application file for complete search history.

(56) References Cited

U.S. PATENT DOCUMENTS

2012/0034464 A1* 2/2012 Chakraborty .......... B82Y 30/00
428/402

OTHER PUBLICATIONS

Bogdanowicz et al.; "Novel Functionalization of Boron-Doped Diamond by Microwave Pulsed-Plasma Polymerized Allylamine Film." The Journal of Physical Chemistry C; American Chemical Society; Mar. 21, 2014; vol. 118, Issue 15; pp. 8014-8025.
Bogdanowicz et al.; "Direct Amination of Boron-Doped Diamond by Plasma Polymerized Allylamine Film." Physica Status Solidi (A); Wiley; Oct. 2014; vol. 211, Issue 10; pp. 2319-2327.
Coffinier, et al.; "Peptide Immobilization on Amine-Terminated Boron-Doped Diamond Surfaces." Langmuir; American Chemical Society; Mar. 17, 2007; vol. 23, Issue 8; pp. 4494-4497.
Hens et al.; "Nanodiamond Bioconjugate Probes and Their Collection by Electrophoresis." Diamond and Related Materials; Elsevier; Nov. 2008; vol. 17, Issue 11; pp. 1858- 1866.
Krueger.; "The Structure and Reactivity of Nanoscale Diamond." Journal of Materials Chemistry; Royal Society of Chemistry; Feb. 25, 2008; vol. 18, Issue 13; pp. 1485-1492.
Krueger et al.; "Functionality is Key: Recent Progress in the Surface Modification of Nanodiamond." Advanced Functional Materials; Wiley; Mar. 7, 2012; vol. 22, Issue 5; pp. 890-906.
Krueger et al.; "Biotinylated Nanodiamond: Simple and Efficient Functionalization of Detonation Diamond." Langmuir; American Chemical Society; Mar. 1, 2008; vol. 24, Issue 8; pp. 4200-4204.
Liu et al.; "Functionalization of Nanoscale Diamond Powder: Fluoro-, Alkyl-, Amino-, and Amino Acid-Nanodiamond Derivatives." Chemistry of Materials; American Chemical Society; Sep. 2, 2004; vol. 16, Issue 20; pp. 3924-3930.
Miller et al.; "Photochemical Modification of Diamond Surfaces." Langmuir; American Chemical Society; Nov. 27, 1996; vol. 12, Issue 24; pp. 5809-5817.

(Continued)

*Primary Examiner* — Hui H Chin
(74) *Attorney, Agent, or Firm* — Thorpe North & Western, LLP

(57) ABSTRACT

A catalytic nanoparticle can include a nanodiamond core, a thin-layer polymeric film applied to an outer surface of the nanodiamond core, and a catalyst immobilized at an outer surface of the thin-layer polymeric film. The nanoparticles can also be used in connection with a transducer to form a sensor. A method of catalysis can include contacting the catalytic nanoparticle with a reactant in a reaction area. The reactant can be capable of forming a reaction product via a reaction catalyzed by the catalyst. The method of catalysis can also include facilitating a catalytic interaction between the catalytic nanoparticle and the reactant.

25 Claims, 16 Drawing Sheets

(56) References Cited

OTHER PUBLICATIONS

Mochalin et al.; "Covalent Incorporation of Aminated Nanodiamond into an Epoxy Polymer Network." ACS Nano; American Chemical Society; Aug. 10, 2011; vol. 5, Issue 9; pp. 7494-7502.
Mochalin et al.; "The Properties and Applications of Nanodiamonds." Nature Nanotechnology; Dec. 18, 2011; vol. 7; pp. 11-23.
Spitsyn et al.; "Inroad to Modification of Detonation Nanodiamond." Diamond and Related Materials; Elsevier; Mar. 2006; vol. 15, Issue 2-3; pp. 296-299.
Strother et al.; "Photochemical Functionalization of Diamond Films." Langmuir; American Chemical Society; Jan. 18, 2002; vol. 18, Issue 4; pp. 968-971.
Szunerits et al.; "Surface Functionalization and Biological Applications of CVD Diamond." CVD Diamond-Research, Applications, and Challenges; MRS Bulletin; Jun. 2014; vol. 39, Issue 6; pp. 517-524.
Wang et al.; "Nanomolar Hydrogen Peroxide Detection Using Horseradish Peroxidase Covalently Linked to Undoped Nanocrystalline Diamond Surfaces." Langmuir; American Chemical Society; Nov. 8, 2011; vol. 28, Issue 1; pp. 587-592.
Zhang et al.; "DNA Micropatterning on Polycrystalline Diamond via One-Step Direct Amination." Langmuir; American Chemical Society; Mar. 18, 2006; vol. 22, Issue 8; pp. 3728-3734.
Zhuang et al.; "Allylamine-Mediated DNA Attachment to Polycrystalline Diamond Surface." AIP; Oct. 2009; vol. 95, Issue 14.

* cited by examiner

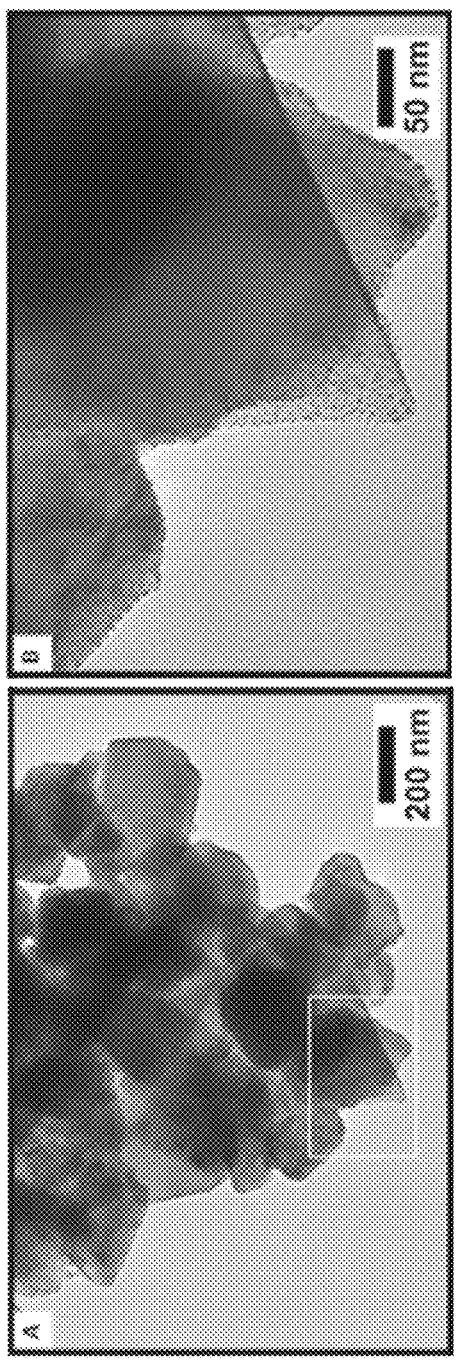
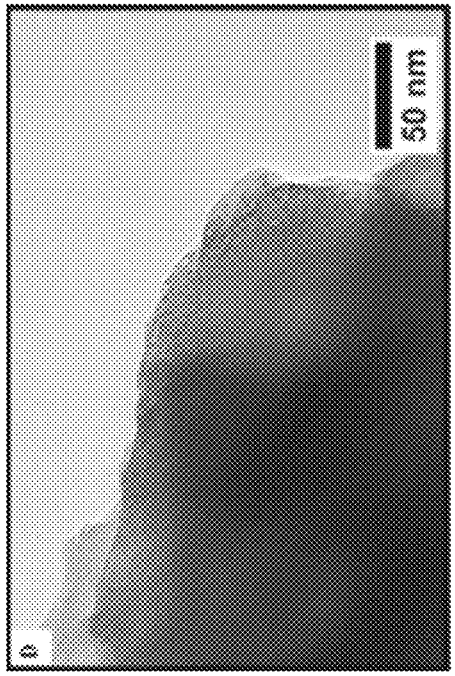
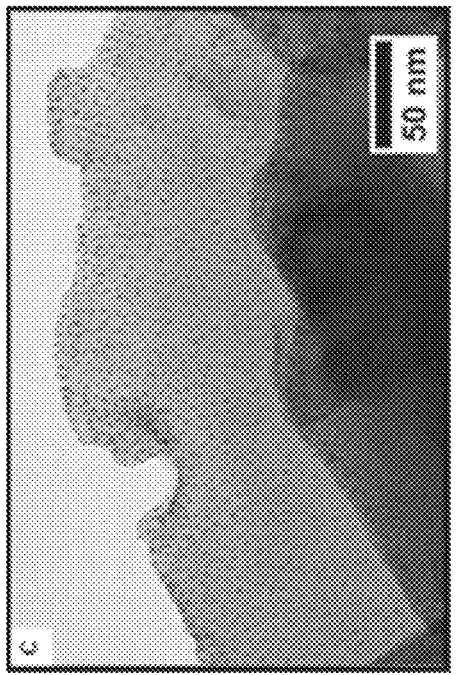
FIG. 2A
FIG. 2B
FIG. 2C
FIG. 2D

NANODIAMOND SUPPORTED CATALYTIC NANOPARTICLES AND ASSOCIATED METHODS

RELATED APPLICATIONS

This application is a continuation-in-part of U.S. patent application Ser. No. 15/625,725, filed Jun. 16, 2017, which claims the benefit of U.S. Provisional Application No. 62/351,177, filed Jun. 16, 2016, each of which is incorporated herein by reference.

GOVERNMENT INTEREST

This invention was made with government support under Grant No. CHE1414466 awarded by National Science Foundation. The government has certain rights in the invention.

BACKGROUND

Ultra-small noble metal nanoparticles (NPs) have become a central topic in nanoscience and catalysis due to the significant differences between the properties of NPs compared to bulk metals. One material exhibiting this behavior is gold, which is inert as a bulk material, yet when prepared as ultra-small NPs, displays remarkable catalytic activity. For example, gold nanoparticles (AuNPs) have been shown to catalyze a variety of reactions including oxidations, reductions, and carbon-carbon bond formation.

Because of the importance of active site availability in heterogeneous catalysis, prevention of particle aggregation can play a significant role in maintaining catalytic efficiency. During catalytic reactions, reactants compete for active surface sites, potentially displacing ligands and eventually leading to unstable high energy surface sites. This, in turn, can cause particle aggregation, reduce catalytic activity, and limit reusability. One approach used to prevent NP aggregation involves the use of a support material that can be a co-catalyst or simply provide mechanical stability during catalytic cycles. Porous and nonporous silica has been widely used because of the ease of modification of the silica surface with mercapto or amino functionalities, which serve as anchor groups for NP attachment. However, the stability of silica-based materials can be compromised in some chemical environments, leading to nanoparticle aggregation and dissolution of the silica support material. Due to such limitations, polymer-supported AuNPs are attractive because in aqueous media they offer significant stability not available with silica supports. However, many reactions require the use of organic solvents where polymeric supports such as polystyrene can swell and dissolve. Thus, depending on the particular application, limitations regarding such supported nanoparticles remain.

SUMMARY

A catalytic nanoparticle can include a nanodiamond core, a thin-layer polymeric film applied to an outer surface of the nanodiamond core, and a catalyst immobilized at an outer surface of the thin-layer polymeric film.

The nanodiamond core can vary in size from 2 nm to 500 nm. However, in some examples, the nanodiamond core can have a size of from about 50 nm to about 500 nm. In other examples, the nanodiamond core size can be from 2 to 10 nm, while in other cases can range from 10 nm to about 100 nm. In some examples, the nanodiamond core can be unhydrogenated. In some examples, the thin polymeric film can have a thickness of from about 1 nm to about 100 nm or about 5 nm to about 20 nm. In some examples, the thin- layer polymer film can include a S—C bond. In some examples, the catalyst can be an enzyme or a ligated ion. In some examples, the catalyst can be a noble metal. In some further examples, the noble metal can be gold, platinum, palladium, silver, rhodium, osmium, iridium, ruthenium, combinations thereof, or alloys thereof. In some examples the catalyst can be immobilized via bonding with a sulfur atom at the outer surface of the thin- layer polymeric film. Alternatively, the catalyst can be immobilized via bonding with a ligand (e.g. a bipyridine tethered to the polymer surface), electrostatic attraction through charged functional groups such as carboxylates or amines, or physical entrapment within the polymer film.

A method of catalysis can include contacting the catalytic nanoparticle with a reactant in a reaction area. The reactant can be capable of forming a reaction product via a reaction catalyzed by the catalyst of the catalytic nanoparticle. The method of catalysis can also include facilitating a catalytic interaction between the catalytic nanoparticle and the reactant.

In some examples, the catalytic nanoparticle can be a heterogeneous catalyst. In some examples, the catalytic nanoparticle can be fixed to a porous material. In some examples, the catalytic nanoparticle can be a homogeneous catalyst. In some examples, the catalytic nanoparticle can be dispersed in a fluid. In some examples, the fluid can be a solution. In some examples, the solution can have a pH greater than or equal to 8. In some examples, the solution can have a pH less than or equal to 5.

A sensor can include a transducer and a catalytic nanoparticle positioned relative to the transducer to facilitate detection of a target analyte. In some examples, the transducer can include an electrochemical transducer, potentiometric transducer, amperometric transducer, conductometric transducer, chemicapacitive transducer, chemiresistive transducer, photoionizing transducer, physical transducer, optical transducer, a biochemical transducer, an affinity-based transducer, a thermochemical transducer, a piezoelectric transducer, or a combination thereof. In some examples, the catalytic nanoparticle can form part of the transducer. In other examples, the catalytic nanoparticle can positioned separate from the transducer. In yet additional examples, the catalyst can include an enzyme, a noble metal, or a combination thereof. In further examples, the noble metal can be a member of the group consisting of gold, silver, and combinations thereof. In some examples, the sensor can further include a light source positioned to direct electromagnetic radiation toward the transducer, the catalytic nanoparticle, or both.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 2A is a TEM image of AuNPs/polymer/ND polymer/ diamond supports, in accordance with one example of the present disclosure.

FIG. 2B is a higher magnification TEM image of the AuNPs/polymer/ND polymer/diamond supports depicted in FIG. 2A.

FIG. 2C is a TEM image of PtNP/polymer/ND polymer/ diamond supports, in accordance with another example of the present disclosure.

FIG. 2D is a TEM image of PdNP/polymer/ND polymer/ diamond supports, in accordance with one example of the present disclosure.

Figure 1A:
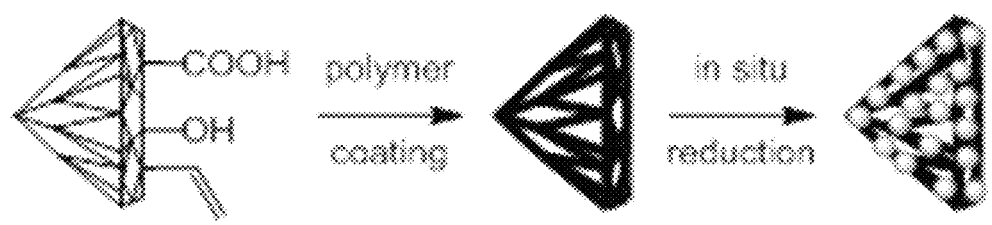
FIG. 1A illustrates an example of a method of decorating a nanodiamond core with metal NPs via in situ reduction of metal salts, in accordance with some examples of the current disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a catalyst" includes reference to one or more of such materials and reference to "contacting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, "unhydrogenated" refers to a surface free of or substantially free of exposed hydrogen. This can include materials which were not previously hydrogenated, as well as material from which surface hydrogen has been removed. In some cases hydrogenated refers to a reduced state while hydroxylated refers to an oxidized state or unhydrogenated state.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "about" is intended to provide a minor amount of flexibility consistent with the variable and context. As a general guideline, about can indicate within 5%, in some cases within 1%, and in some other cases within 0.1%. In any circumstance, the term "about" also expressly includes exactly the value indicated.

As used herein, the term "at least one of" is intended to be synonymous with "one or more of" For example, "at least one of A, B and C" explicitly includes only A, only B, only C, and combinations of each (e.g. A+B, B+C, A+C, and A+B+C).

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub- range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Catalytic Nanoparticles and Associated Methods

Much research has been done using polymer and silica particles as support materials for catalytically-active noble metal nanoparticles, but these materials have limited stability in organic solvents or under extreme reaction conditions such as high pH. In an effort to address the stability challenges of metal nanoparticles and develop a versatile and robust catalytic platform, a polymer-diamond composite material was investigated that can offer high mechanical and chemical stability in diverse environments. By coating synthetic diamond particles with a thin polymer adhesion layer, a scaffold can be formed for high surface density deposition of ultra-small metal nanoparticles (NPs) with high catalytic activity. The polymer-diamond support exhibits enhanced stability compared to silica particle supports offering access to reactions and conditions that were previously limited by support material stability and reaction environment incompatibility.

Thus, a robust and versatile composite polymer-diamond support for ultrasmall noble metal nanoparticles and other catalysts is described herein. This catalytic nanoparticle demonstrates the combined chemical and mechanical stability of diamond with the chemical versatility of a polymer. More specifically, the catalytic nanoparticle can include a nanodiamond core, a thin-polymeric film applied to an outer surface of the nanodiamond core, and a catalyst immobilized at an outer surface of the thin-layer polyermic film.

The nanodiamond core of the catalytic nanoparticle can have a range of suitable sizes. However, it can be beneficial to keep the nanodiamond core within a suitable size range to maintain a sufficiently high surface area for the catalytic nanoparticle. Thus, the nanodiamond core can have a size from 0.001 µm to 2 µm, and typically have a size of from about 50 nm to about 500 nm, or from about 100 nm to about 300 nm.

Further, nanodiamond (ND) offers chemically and mechanically robust nanoparticles with reactive functional groups at their surface. It is noted that $sp^2$ carbon atoms in a graphitic shell cover the core $sp^a$ carbon atoms of the diamond inside the graphitic shell. The surface of the ND particles can contain such functionalities as vinyl, hydroxyl and carboxylic acid groups that can be modified under a variety of conditions. However, for certain applications, the degree of functionality on the surface of the nanodiamond can still be less than desirable. One potential solution to the lack of functionality of the nanodiamond can be to hydrogenate the nanodiamond, thus increasing the functionality of the nanodiamond surface. Nanodiamond hydrogenation can be performed using a variety of suitable techniques, and any suitable technique is considered within the scope of the present disclosure. Non-limiting examples can include plasma- assisted hydrogenation, annealing under hydrogen flow, the like, or a combination thereof. In other examples, the nanodiamond core can include sufficient functionality without hydrogenation and the nanodiamond core can be unhydrogenated. In some examples, the diamond manufacturing process can also leave traces of iron or other carbide forming residues from the molten solvent used to manufacture the diamond, which can also increase the functionality of the nanodiamond surface.

Alternatively, aminated nanodiamond can be prepared using any number of suitable techniques. In addition to the use of aminosilanes to modify diamond surface, amination of diamond can be carried out using a variety of methods. For example, 70 minutes of exposure to 1-3 L/hr anhydrous ammonia at 1 atm and 850° C. can successfully reduce surface oxygen content with a corresponding increase in nitrogen attributed to direct attachment of primary amines to the diamond surface. This method can also result in removal of graphitic surface impurities during amination by reduction of these non-diamond carbon atoms to form HCN(g). Another amination approach includes photochemical modification of the diamond surface in a two-step process to produce $NH_2$-terminated diamond. Chlorinated diamond (formed using $Cl_{2(g)}$ in CVD) can be reacted under UV irradiation in an atmosphere of ammonia gas. Also, plasma assisted direct amination of H-terminated diamond can be used in a one step attachment of biological materials. Direct modification of H-terminated diamond can also be performed using tert- butoxycarbonyl (t-BOC) protected amino-alkenes using UV illumination. Allylamine attachment has also been shown to be effected using either plasma polymerization or UV illumination. Wet chemistry methods can also be used for amination of diamond surfaces by starting with hydroxylated diamond to prepare aminated diamodiamond. Specifically, tosylation of surface hydroxyl groups can be followed by substitution with nitrile moieties which can then be reduced using lithium aluminum hydride to form aminomethyl groups. In another alternative, $F_{2(g)}$ at 310° C. through the use of CVD to fluoronate diamond which was then reacted with diamines such as ethylenediamine. In still another two-step example, amination of diamond can be accomplished by refluxing fluoro-terminated diamond in a mixture of EDA and pyridine at 130° C. for 24 hr under nitrogen.

As such, a variety of surface groups can be used to anchor a thin-layer polymeric film to an outer surface of the nanodiamond core. This can be done with the intention of creating a scaffold for immobilization of metal nanoparticles. Thus, by exploiting the rich surface chemistry of nanodiamond and coating the nanodiamond with a polymeric material, a thinly-coated polymer-diamond composite can be formed.

In some examples, the nanodiamond and polymeric material can be combined at a predetermined weight ratio. This can help provide a homogenous distribution of nanodiamond/polymer composite support structures for immobilization of a catalyst thereto. For example, in some cases, the nanodiamond and polymeric material can be combined at a weight ratio of from about 100:1 to about 0.8:1, and in some cases 100:1 to 10:1. In other cases the proportion of polymer can be higher such as about 3:1 to about 0.8:1 nanodiamond to polymeric material. In yet other examples, the nanodiamond and polymeric material can be combined at a weight ratio of from about 2:1 to about 1:1, or about 1.8:1 to about 1.2:1 nanodiamond to polymeric material.

Further, in some examples, it can be desirable to maintain a thin-layer polymeric film of minimal thickness. This can help provide a more uniform surface for the immobilization of a catalyst at an outer surface of the thin-layer polymeric film. Further, by keeping the thickness of the thin-layer polymeric film small the surface area for the catalytic nanoparticles can remain higher. Therefore, the thin-layer polymeric film can have a thickness of from about 1 nm to about 100 nm, about 3 nm to about 30 nm, or about 5 nm to about 20 nm.

With the high robustness of the diamond and the ability to tailor the monomer combinations, this polymer-diamond support system can be expanded to a wide range of nanoparticle compositions suitable for various reaction conditions. A variety of monomers and/or polymers can be used to prepare the thin-layer polymeric film on the surface of the nanodiamond core. In one non-limiting example, thiol-ene chemistry can be suitable for chemical modification of ND surfaces. Accordingly, the thin-layer polymeric film can be formed using a monomer or polymer having a pendant thiol group, a terminal thiol group, or a combination thereof. Thus, in one example, the thiol group of the polymer or monomer can be reacted with an alkene group or other suitable moiety on the surface of the nanodiamond or an additional monomer to generate a sulfur-carbon (S—C) bond. Therefore, the thin-layer polymeric film can include a polymer having an S—C bond. In some specific examples, the polymer can be attached to the nanodiamond core via an S—C bond. In additional examples, a first monomeric unit of the polymer can be attached to a second monomeric unit of the polymer via an S—C bond. Again, this is only one representative example of a chemistry that can be used to connect individual monomers of the polymer and/or attach the polymer to the nanodiamond core. Other suitable chemistries can also be employed in addition to or separate from thiol-ene chemistry. For example, C—C bonding via alkene/alkyne chemistries, amine-carboxylate, amine aldehyde via imine chemistries, among others which are known to those skilled in the field can also be employed between monomeric units and/or to attach the polymer to the nanodiamond core.

With this in mind, and as described above, a variety of suitable monomeric units can be employed in the polymeric film coated onto the nanodiamond core. Non-limiting examples of suitable monomers can include thiolenes, thiolynes, amides, silanes, imines, amides, cyanates, isocyanates, and other polymers which act as adhesion promoters with nanodiamond. The polymeric film is not particularly limited. The monomer units can provide the ability to produce a polymerized film in addition to functional groups available for tethering catalysts, as well as a functional groups for adhesion to the nanodiamond core.

In some specific examples, the polymer can include pentaerythritol tetra(3-mercaptopropionate) (PETMP). In some additional examples, the polymer can include triallyl-1,3,5-triazine-2,4,6-trione (TATATO). In yet other examples, the polymer can include N-(3-Aminophropyl)methacrylamide hydrochloride (APMAA). In still additional examples, the polymer can include 2-aminoethyl methacrylate hydrochloride (AEMA). In some examples, the polymer can include PETMP, TATATO, APMAA, AEMA, or a combination thereof. In some specific examples, the polymer can include PETMP, TATATO, and APMAA. In yet other specific examples, the polymer can include PETMP, TATATO, and AEMA. In the case of TATATO:PETMP a molar ratio can be about 4:3 and in some cases within about 10% of 4:3.

It is further noted that thiol-ene polymers can also be effective for adhesion of catalytic NPs to the surface of the ND. More specifically, in some examples, thiol-ene chemistry can be used for attachment of a thin-layer polymeric film to a ND and subsequent immobilization of catalysts to the thin-layer polymeric film. In yet other examples, the polymer can be attached to the nanodiamond core via thiol-ene chemistry, whereas the catalyst can be immobilized to the polymeric film via an alternative chemistry. In still other examples, the catalyst can be immobilized to the polymeric film via thiol-ene chemistry, whereas the polymeric film can be attached to the nanodiamond core via an alternative chemistry. Therefore, in some examples, the catalyst can be immobilized via bonding with a sulfur atom at the outer surface of the thin-layer polymeric film. It is further noted that in some cases the polymeric film can be attached to the nanodiamond via a variety of chemistries, such as thiol-ene chemistry in combination with one or more additional chemistries, for example. Further, in some examples, the catalyst can be immobilized to the polymeric film via a variety of chemistries, such as thiol-ene chemistry in combination with one or more additional chemistries. Non-limiting examples can include electrostatic interactions between amines and metallic nanoparticles, physical entrapment, thiolate bonding, ligand bonding (e.g. phosphines, amines, thiols, carboxylic acids, etc), and the like.

A variety of catalysts can be immobilized at an outer surface of the thin-polymeric film. In one example, the catalyst can be an enzyme or combination of enzymes. In another example, the catalyst can be a noble metal. Noble metal catalysts can include gold, platinum, palladium, silver, rhodium, osmium, iridium, ruthenium, the like, alloys thereof, or combinations thereof. In other examples, a combination of one or more types of enzymes can be used with one or more types of noble metal catalysts or other catalysts.

In yet another alternative, the catalytic nanoparticles can include stabilizing ligands on outer surfaces of the catalytic particles. Suitable stabilizing ligands can include those that facilitate a stable dispersion within specific environments (e.g. aqueous versus non-aqueous solutions). Non-limiting examples of suitable stabilizing ligands can include thiols, phosphines, amines, carboxylic acids, and the like.

The catalytic nanoparticles described herein can be used in a method of catalysis. More specifically, the catalytic nanoparticle can be brought into contact with a reactant in a reaction area. The reactant can be any reactant capable of forming a reaction product via a reaction catalyzed by the catalyst of the catalytic nanoparticle. There are various methods of contacting the catalytic nanoparticle with the reactant. In one example, the catalytic nanoparticle can be a heterogeneous catalyst. As such, the catalytic nanoparticle can be immobilized to a solid substrate and a fluid including the reactant can be brought into contact with the catalytic nanoparticle so as to allow the reactant to adsorb onto the catalytic nanoparticle. The fluid can be a gas, a liquid, or a combination thereof. In one example, the catalytic nanoparticle can be fixed to a porous material across which or through which the reactant fluid flows, thus bringing the reactant into contact with the catalytic nanoparticle. In other examples, catalytic nanoparticles can form at least a part of a packed reaction bed through with the reaction fluid is passed, thus bringing the reactant into contact with the catalytic nanoparticle.

In other examples, the catalytic nanoparticle can be a homogeneous catalyst. In this case, the catalytic nanoparticle can be dispersed in a reaction fluid. As the catalytic nanoparticle is dispersed throughout the reaction fluid it can come into contact with the reactant and catalyze the production of a reaction product in the fluid. In some examples, the reaction fluid can be a solution. Due to the stability of the disclosed catalytic nanoparticles, they can be used in a broad range of reaction environments previously limited by support material stability and reaction environment incompatibility. As such, in some examples, the solution can have a pH of greater than or equal to 8, greater than or equal to 10, greater than or equal to 12, or greater than or equal to 14. In other examples, the solution can have a pH of less than or equal to 5, less than or equal to 3, or less than or equal to 1.

The method of catalysis can also include facilitating a catalytic interaction between the catalytic nanoparticle and the reactant. This can be done in a number of ways. In some examples, facilitating a catalytic interaction can include adjusting the pH of the reaction fluid to a suitable pH for catalysis. In some examples, facilitating a catalytic interaction can include adjusting a temperature of the reaction fluid to a suitable temperature for catalysis. In some examples, facilitating catalytic interaction can include adjusting the ionic strength or tonicity of the reaction fluid. In some examples, facilitating a catalytic interaction can include adequately mixing the reaction fluid and/or catalytic nanoparticle to increase the interaction therebetween. In some examples, facilitating a catalytic interaction can include directing the flow of the reaction fluid toward and/or across the catalytic nanoparticles. In some examples, facilitating a catalytic interaction can include providing a co-catalyst necessary for or beneficial to catalysis of a desired reaction. Other parameters can also be adjusted or employed to facilitate a catalytic interaction between the catalytic nanoparticle and the reactant, such as introduction of electromagnetic radiation, or any other suitable parameter.

The catalytic nanoparticles can be used as catalyst in aqueous, polar, or nonpolar solutions. The coating on the diamond can also be tailored using different monomers for a variety of reaction environments. As such, this material would be suitable for any catalytic reaction requiring a homo/heterogeneous metallic/nonmetallic catalyst.

For example, the catalytic nanoparticles described herein can also be incorporated into a sensor. The sensor can include a transducer and a catalytic nanoparticle operatively associated with and/or positioned relative to the transducer to facilitate detection of a target analyte. In some examples, the catalytic nanoparticle can form part of the sensor transducer. In yet other examples, the catalytic nanoparticle can be introduced and/or positioned to interact with an analyte to facilitate detection of the analyte by the transducer. For example, the catalytic nanoparticles can introduced and/or positioned to catalytically interact with a target analyte to generate a product analyte that is detectable by the sensor transducer. In some examples, the catalytic nanoparticles can be immobilized or dispersed within a fluid channel so as to interact with a target analyte before it reaches a transducer. Thus, in some examples, the catalytic nanoparticles can be positioned away or separate from the transducer to facilitate detection of the analyte by the transducer.

The sensor can include a variety of transducers, such as electrochemical transducer, potentiometric transducer, amperometric transducer, conductometric transducer, chemicapacitive transducer, chemiresistive transducer, photoionizing transducer, a physical transducer, an optical transducer, a biochemical transducer, an affinity-based transducer, a thermochemical transducer, a piezoelectric transducer, any other suitable transducer, or a combination thereof. In some specific examples, the transducer can be or include an electrochemical transducer, biochemical transducer, affinity-based transducer, optical transducer, piezoelectric transducer, or a combination thereof. In some additional examples, the transducer can be or include a potentiometric transducer, amperometric transducer, conductometric transducer, chemicapacitive transducer, chemiresistive transducer, or a combination thereof.

In some specific examples, the sensor can be a biosensor. In some examples, the immobilized catalyst of the catalytic particle employed by the biosensor can be or include a noble metal catalyst. In some further examples, the immobilized catalyst of the catalytic nanoparticle can be or include one or more enzymes. In some examples, the enzyme can convert a target analyte into a product analyte that is detectable by the biosensor transducer. In other examples, the enzyme can inhibit or activate an analyte such that the inhibited or activated analyte is detectable by the biosensor transducer. In yet other examples, at least one property of the enzyme, such as electrical charge, for example, can be directly detected due to interaction with a target analyte. As such, in some examples, the enzyme can form part of the biosensor transducer. In some examples, the catalytic nanoparticle of the sensor can be immobilized to a solid substrate of the sensor and a fluid including the analyte can be brought into contact with the catalytic nanoparticle so as to allow the analyte to adsorb onto the catalytic nanoparticle. In yet other examples, the catalytic nanoparticle of the sensor can be dispersed within or throughout the sensor such that it can come into contact with the analyte to facilitate detection of the analyte. The readout for the sensor could be production of a photoactive agent for detection using absorption or emission spectroscopy. In another example the readout could be electrochemical in the case of an electrochemically active product.

In another specific example, the sensor can be a plasmonic sensor. In some further examples, the immobilized catalyst of the catalytic nanoparticle can be or include one or more noble metal catalysts. In some specific examples, the noble metal catalyst can be or include Au, Ag, or a combination thereof. As will be recognized by one skilled in the art, when light is incident on a metal nanoparticle, such as the metal catalyst, it makes the conduction electrons within the metal nanoparticle oscillate with a resonant frequency. These oscillations can be a function of the shape, size, and morphology of the metal nanoparticle. Thus, the metal nanoparticles can absorb and scatter light very intensely. Accordingly, in some examples, an analyte can be labeled with a catalytic nanoparticle as described herein. In such examples, the strong light absorption and/or scattering due to the catalytic nanoparticle label can be optically detected. In some other examples, where the analyte is not labeled with the catalytic nanoparticle, a change in light absorption and/or scattering due to an interaction of the catalytic nanoparticle with a target analyte can also be detected. Thus, the sensor can be adapted to detect a variety of changes in refractive index due to catalytic interaction between the target analyte and the catalytic nanoparticle. In some examples, the catalytic nanoparticle of the sensor can be immobilized to a solid substrate of the sensor and a fluid including the analyte can be brought into contact with the catalytic nanoparticle so as to allow the analyte to adsorb onto the catalytic nanoparticle. In some examples, the catalytic nanoparticle can form part of the transducer. In some additional examples, the catalytic nanoparticle of the sensor can be dispersed within or throughout the sensor such that it can come into contact with the analyte to facilitate detection of the analyte.

In addition to the biosensor and plasmonic sensor described herein, a variety of additional sensors and sensor types can also include and/or employ the catalytic nanoparticles described herein. Further, in some examples, the sensor can include a variety of additional components, such as a housing, fluidic channels positioned to direct an analyte toward the catalytic nanoparticle and/or the transducer, an inlet for introducing an analyte and associated media into the sensor, an outlet for collecting and/or exhausting an analyte and associated media from the sensor, a light source to direct electromagnetic radiation toward the catalytic nanoparticle and/or a target analyte, an actuator/indicator (such as an LED, audible alarm, computer, display, etc.), a communications module to transmit data via a physical connection and/or wireless connection to a connected and/or remote device, a power module, a data collection module, a processor, and/or any other suitable hardware and/or software.

EXAMPLES

A variety of reagents were used in the following examples. Such reagents include Pentaerythritol tetra(3-mercaptopropionate) (PETMP), triallyl-1,3,5-triazine-2,4,6-trione (TATATO), 2,2-dimethoxy-2-phenylacetophenone (DMPA), N-3-dimethylaminopropyl)-N'-ethylcarbodiimide HCl (EDAC), pentafluorophenol (PFP), triethylphosphine gold (I) chloride, chloroplatinic acid hydrate, bis(triphenylphosphine)palladium(II) dichloride, triphenylphosphine (TPP), sodium borohydride ($NaBH_4$), 4-nitrophenol (PNP), 0.5 M THF solution of 9-Borabicyclo[3.3.1]nonane (9-BBN), and isopropanol (IPA) were obtained from Sigma-Aldrich. N-(3-Aminophropyl)methacrylamide hydrochloride, >98% (APMAA) and 2-aminoethyl methacrylate hydrochloride, 95% (AEMA) were purchased from Polysciences, Inc. Reagent grade acetonitrile (ACN), methylene chloride, chloroform, hexanes, toluene, and acetone were purchased from Fisher Scientific. Ethyl alcohol (200 proof) was purchased from Decon Labs. Methanol was purchased from Omni Solve. (3-Mercaptopropyl)trimethoxysilane (MCPTMS), 95% was purchased from Alfa Aesar. Rhodamine B, 98% was purchased from Acros Organics. Dansyl chloride, ≥99.0 was purchased from Fluka. Aqueous solutions of 10% monocrystalline diamond powder (MDP(N)) produced by the belt type press method using a nickel/iron catalyst were purchased from Advanced Abrasives Corp. All water used was obtained from a Barnstead Diamond Nanopure system with a resistivity ≥18.0 MΩ·cm. All reagents were used without further filtration or purification. For TEM imaging copper formvar/carbon grids (200 mesh) were acquired from Electron Microscopy Sciences.

Example 1

Preparation of Polymer-Coated Diamond Supported AuNPs

The following reagents were mixed vigorously and added in the order listed to prevent premature polymerization from uninhibited monomers. Approximately 0.2 g of 0.25 µm MDP diamond (2 g of 10% diamond solution in water as provided by the manufacturer) was mixed with the following: 2.8 g ACN, 5.8 g water, 0.0002 g $Et_3AuCl$, 0.04 g PETMP, 0.08 g TATATO, 0.014 g APMAA or AEMA, and 0.00537 g DMPA. The combined solution was mixed vigorously for at least 30 minutes prior to exposure to UV light. The mixture was then exposed to a UV lamp for 1 hour while mixing. More specifically, curing solutions were stirred at an approximate distance of 5 inches from a 15 Watt Ultra Violet Products (UVP) XX-15S 254 nm benchtop lamp.

Figure 1B:
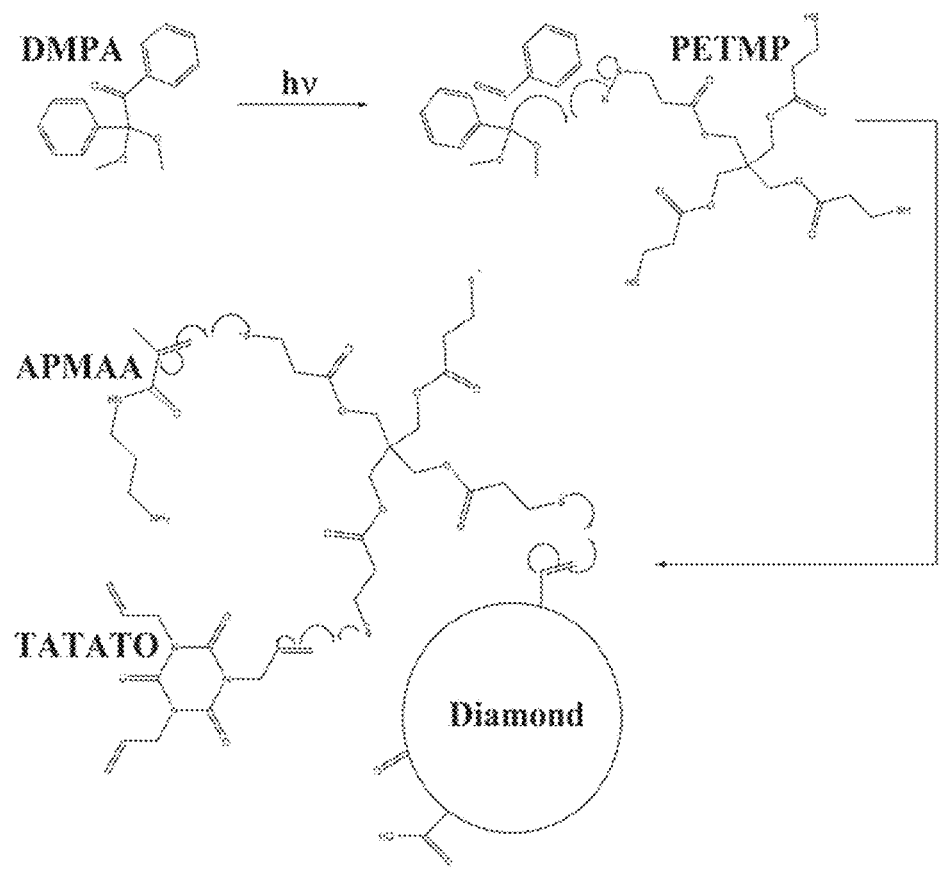
FIG. 1B illustrates an example of a reaction scheme for decorating a nanodiamond core with metal NPs via in situ reduction of metal salts, in accordance with some examples of the current disclosure.

In this process, the photo-initiator DMPA can be exposed to UV light at 254 nm, generating free radicals that cleave the S—H bonds in PETMP, which then combine with vinyl monomers present in solution and with the double bonds present on the ND surface (FIG. 1A). Although TATATO monomer is commonly used for this purpose, monomers including primary amine groups, such as AEMA and/or APMAA monomers, can also be used. A mechanism for this polymerization process is illustrated in FIG. 1B.

After curing, the solution was centrifuged and the solid was rinsed with copious volumes of IPA and ACN. The resulting solids were then mixed with 5.0 mL of 0.130 molal Et$_3$PAuCl in ACN overnight. While mixing, over the course of 10 minutes, 10 drops of an aqueous 0.1 M NaBH$_4$ solution was added and the solution was allowed to continue mixing for >24 hours. The resulting solids were then rinsed with copious amounts of H$_2$O, IPA, and then stored in IPA. The amount of Et$_3$PAuCl was increased or decreased to obtain the desired catalyst loading and the same method was used for equimolar solutions of Pt and Pd salts. As a general guideline, catalyst loading can vary from 0 to 70% mass, and often from 0.1 to 30% mass. APMAA and/or AEMA were included only if primary amines were to be incorporated into the polymer coating.

Initially, polymerization was attempted on the surface of NDs followed by immobilization of metal NPs. However, the resulting composite material was highly inhomogeneous with most of the NDs being either sparsely covered with metal NPs or completely lacking any surface bound NPs. Additionally, polymer films did not possess consistent thickness or surface coverage. ND particles were either not coated with polymer or large polymer masses were found to encase many NDs. These observations led to modified preparation methods in an effort to achieve a more homogeneous mixture of metal NPs, polymer, and ND. It was discovered that when the metal NP precursor salts were present in the reaction mixture, more uniform polymeric films were formed on the ND surface. As a result, this approach was followed to prepare the metal particle catalysts on the polymer-coated ND.

Example 2

Transmission Electron Microscopy (TEM) of Catalytic Nanoparticles

As described above, upon treatment with sodium NaBH$_4$, gold (Au), platinum (Pt), and palladium (Pd) NPs were immobilized on the surface of the polymer-coated NDs. These catalytic nanoparticles were analyzed via TEM as follows.

TEM images were collected using a JEOL 1400 plus with an accelerating potential of 120 kV and a LaB$_6$ thermionic source. Determination of particle diameters was limited due to the irregularity and thickness of the diamond supports. Consequently, the EM images exhibit large changes in contrast. This made flat-field correction of the images difficult and as a result particle counts were lower than desirable. Manual determination of particle diameters resulted in greatly reduced uncertainties when compared to image software particle analysis.

Single-axis tilt images were obtained using automated EM data acquisition with SerialEM software with 1° changes between images for a total of 116°. The series of images was then processed to correct alignment errors using IMOD 4.7.

FIG. 2 shows TEM images of Au, Pt and Pd NPs on polymer-coated ND supports. The roughly 200 nm ND particles appear to form large agglomerates, however, this aggregation is mainly due to the drying process in TEM sample preparation. These agglomerates are easily dispersed in solution using ultrasonication. A closer inspection of these NDs (FIG. 2B) shows AuNPs with a diameter of ~3 nm on the polymer/diamond surface. As seen in FIG. 2B, the AuNPs follow the contour of the diamond support closely, suggesting that the polymer adhesion layer is thin.

In addition to Au, in situ particle growth worked for the formation of Pt and Pd NPs, as can be seen in FIGS. 2C-2D. The ability to incorporate different metals demonstrates the versatility of the polymer/diamond composite as a support material. Several factors were found to influence the NP growth: the concentration of NaBH$_4$ added to the metal salt seeded polymer/NDs, the rate at which the NaBH$_4$ was added to the mixture, the concentration of metal salt, and the temperature of the mixture at the time of NP growth.

Example 3

Thermogravimetric Analysis (TGA) and Brunauer-Emmett-Teller (BET) Surface Area

TGA measurements were performed on a TA Instrument, Hi-Res TGA 2950 Thermogravimetric Analyzer. A Micromeritics ASAP-2020 analyzer was used to measure BET surface area by nitrogen adsorption and desorption isotherms at −195.6° C. after the sample was degassed in vacuum at 250° C. for 3 h.

Figure 3:
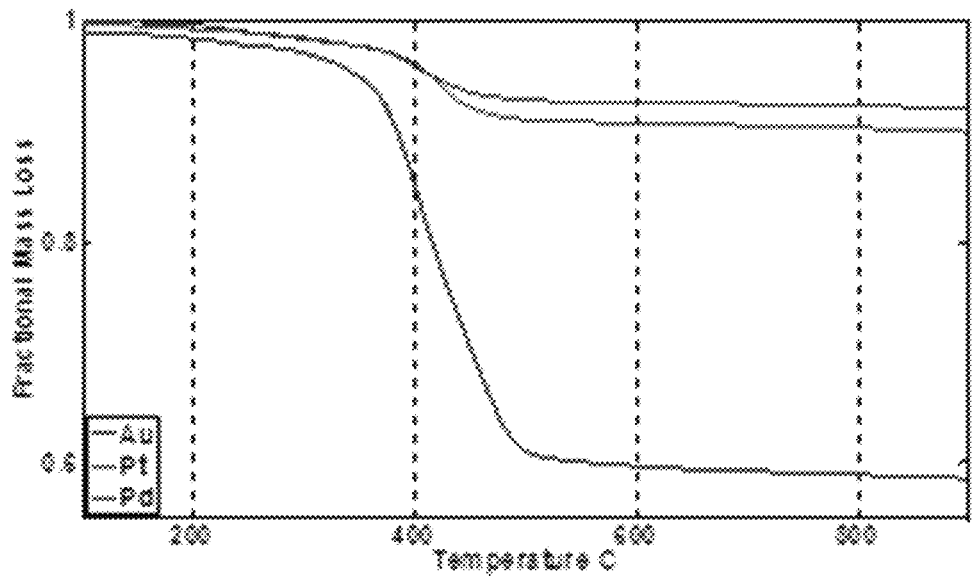
FIG. 3 is a graph of data collected during a thermogravimetric analysis (TGA) of thiol-ene polymer/ND composites supporting either Au, Pt, or Pd NPs obtained to confirm the presence of the polymer. Mass loss curves show that the onset of polymer decomposition occurs at ~350° C. and continues until ~500° C.

The presence of the polymer layer on the surface of NDs was confirmed by TGA, (See FIG. 3), which showed a mass fraction of the polymer in the NP/polymer/NDs of 0.4 for AuNPs and of 0.1 for Pt and Pd NPs. The following relationship was used to convert the mass fraction to an average polymer thickness:

$$P_{thick} = \frac{m_p S_d}{\rho_p} \quad [1]$$

where $P_{thick}$ (nm) is the polymer thickness, $m_p$ (unitless) is the mass fraction of polymer per gram of diamond, $S_d$ (nm$^2$/g) is the surface area of the ND, and $\rho_p$ (g/nm$^3$) is the density of the polymer. Using an average polymer density of 1.2 g/cm$^3$ (1.28 g/cm$^3$ for PETMP and 1.1590 g/cm$^3$ for TATATO), ND density of 3.513 g/cm$^3$, and BET specific surface area for ND of 19.5 m$^2$/g, the thickness of the polymer films can be estimated as ~29 nm for the Au/polymer/ND and ~5 nm for the Pt/polymer/ND and Pd/polymer/ND. Although TEM is capable of sub-nm resolution, the polymer adhesion layer is not visible in the TEM images shown in FIG. 2. This is likely the result of drying and shrinking of the polymer in the high vacuum environment of the TEM, as well as the low polymer density.

Example 4

Diffuse Reflectance Infrared Fourier Transform Spectroscopy (DRIFTS)

A PIKE Technologies DiffusIR accessory was attached to a Perkin-Elmer Spectrum 100 FTIR for DRIFTS data collection. Powdered samples were diluted with KBr powder and spectra were acquired by averaging 64 scans with the resolution set to 4 cm$^{-1}$.

Figure 4A:
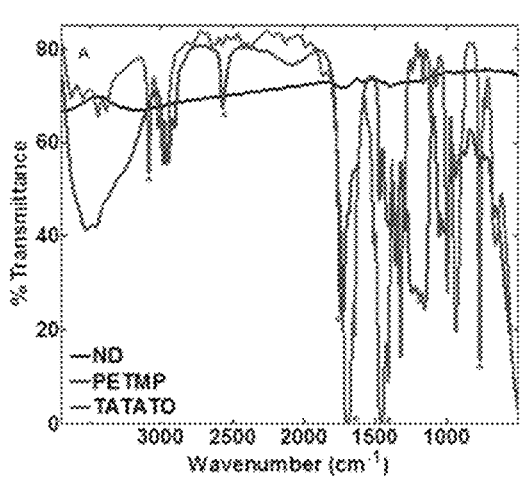
FIG. 4A is a graph of vibrational spectra of monomers (neat films on NaCl) and diamond (dried powder diluted with KBr) probed by DRIFTS. Asterisks indicate features similar between monomers and polymer/NDs.
Figure 4B:
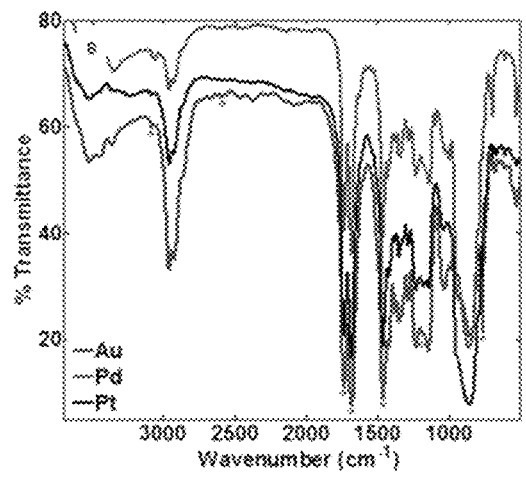
FIG. 4B is a DRIFTS spectra for polymer/NDs with imbedded Au, Pd, or Pt NPs. Asterisks indicate features similar between monomers and polymer/NDs.

The presence and composition of the polymer layer were confirmed by DRIFTS. The spectrum for the bare NDs is smooth and featureless as expected, while the principle monomers have several identifying features above 1500 cm$^{-1}$ in addition to those in the fingerprint region (FIG. 4A), such as carbonyl peaks characteristic of the PETMP and TATATO monomers at 1738 cm$^{-1}$ and 1688 cm$^{-1}$, respectively. These same carbonyl peaks are observed in the composite particles (FIG. 4B) indicating that the PETMP and TATATO were incorporated into the polymer. Furthermore, because the molar ratio of PETMP:TATATO is 3:4, the carbonyl peaks in the DRIFTS spectra of polymer/NDs have similar intensities. Other characteristic peaks are located at 3085 cm$^{-1}$ (weak), 1466 cm$^{-1}$ (strong, sharp), 765 cm$^{-1}$ (sharp) in the IR spectra of the composite particles and in the IR spectrum of pure PETMP. The thiol peak at 2600 cm$^{-1}$ is well resolved in the spectrum of pure PETMP but not in the spectra of the composite particles. The absence of the S—H vibrational mode in the composite particles can be a result of the oxidation of sulfur, bonding to metal clusters, and/or low concentration. However, the thiol region is typically very weak in materials that contain S—H bonds and its absence is not unexpected. Finally, three peaks centered at 1185 cm$^{-1}$ are present in the composite particles as well as the IR spectrum of pure TATATO.

Example 5

X-ray Photoelectron Spectroscopy

Data was collected using a Kratos Axis Ultra DLD system. Monochromatic Al K-alpha X-Rays were used (1486.6 eV), with a power of 150 W (10 mA emission current, 15 kV on the anode). The base pressure in the analysis chamber was 8×10$^{-10}$ Torr. All spectra were collected over an analysis area of approximately 300×700 microns (as defined by the hybrid/slot settings on the systems lens mode and aperture settings). For high and low resolution spectra, the hemispherical analyzer was operated in FAT (Fixed Analyzer Transmission) mode. Charging artifacts in the spectra were minimized using the systems charge neutralizations system. Wide energy region survey spectra and high resolution regional spectra were collected using pass energies of 160 eV and 40 eV, respectively.

Figure 5A:
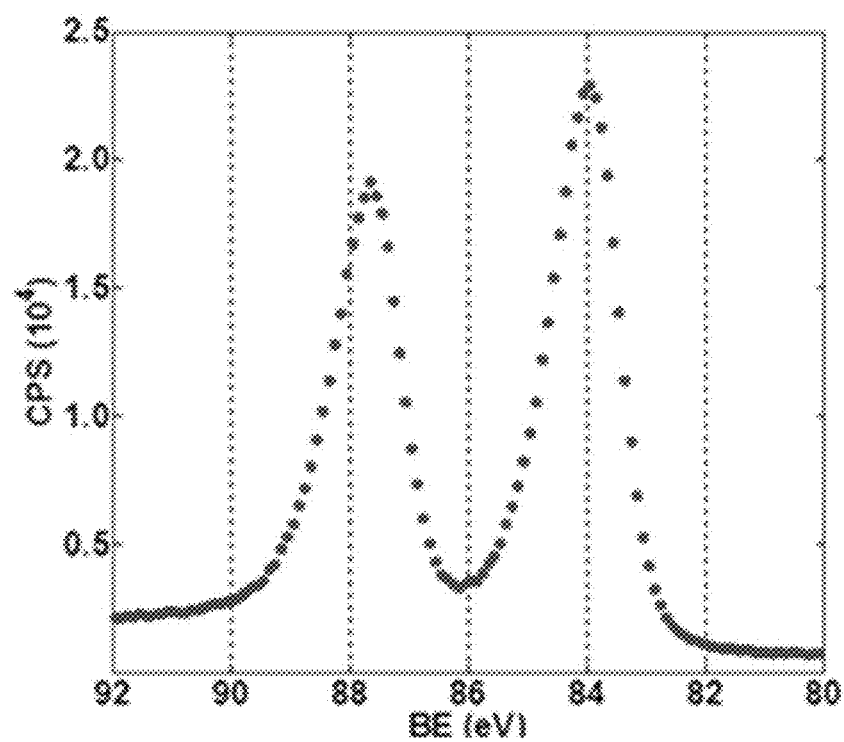
FIG. 5A is an XPS spectra of the Au 4f region of AuNP/polymer/NDs, in accordance with an example of the present disclosure.
Figure 5B:
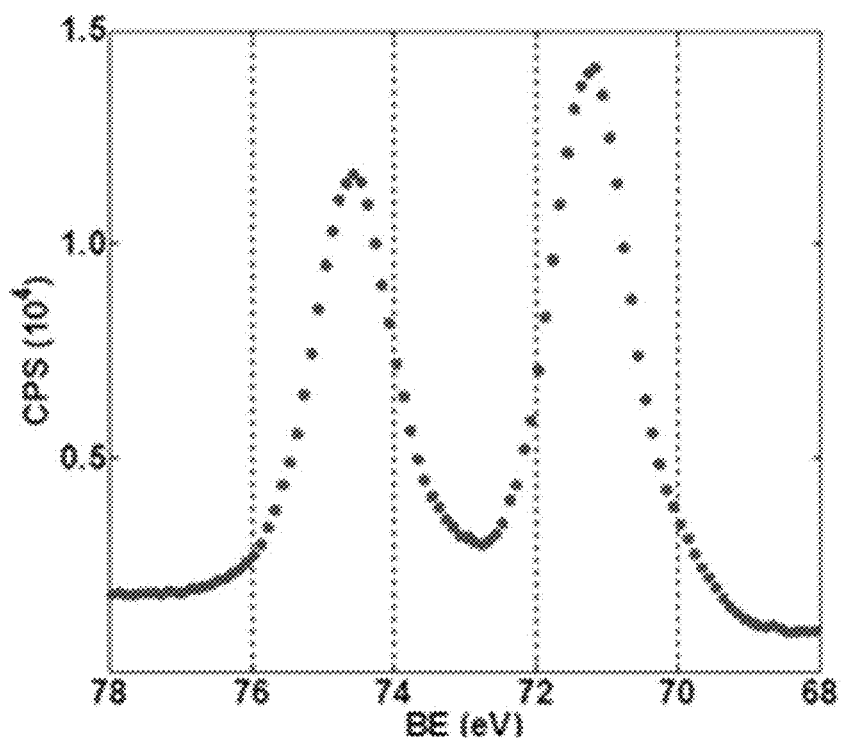
FIG. 5B is an XPS spectra of the Pt 4f region of PtNP/polymer/NDs, in accordance with an example of the present disclosure.
Figure 5C:
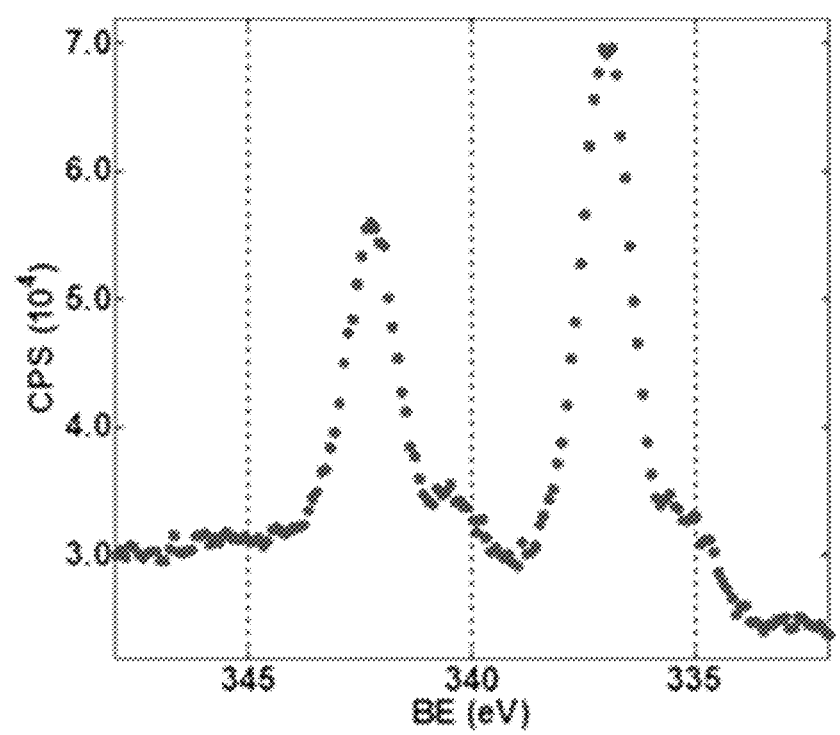
FIG. 5C is an XPS spectra of the Pd 3d region of PdNP/polymer/NDs, in accordance with an example of the present disclosure.
Figure 5D:
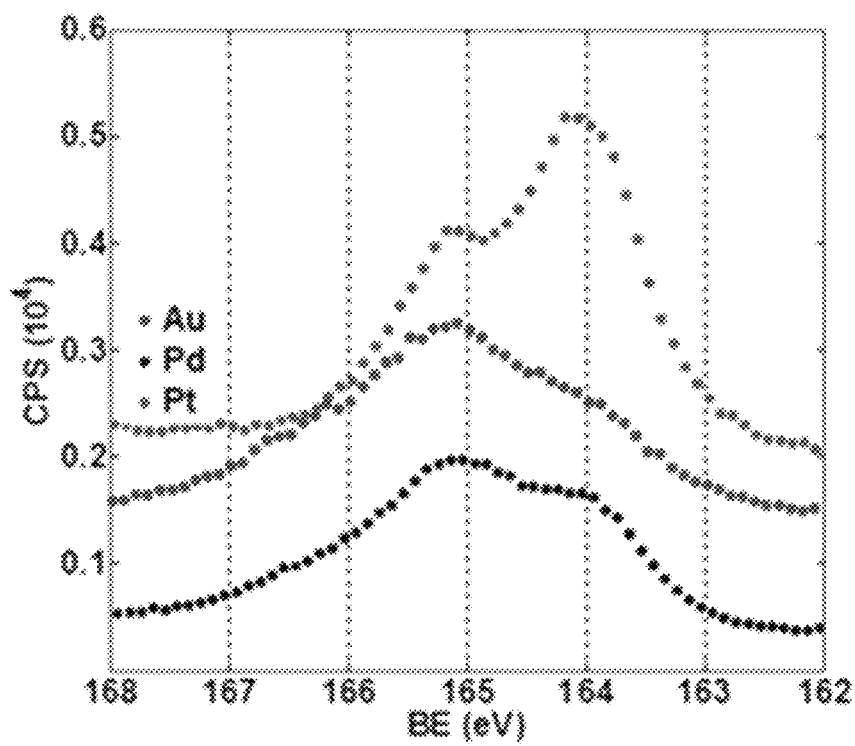
FIG. 5D is a stacked XPS spectra for the S 2p region for AuNP/polymer/NDs, PtNP/polymer/NDs, and PdNP/polymer/NDs, in accordance with certain examples of the present disclosure.

X-ray photoelectron spectroscopy (XPS) analysis confirmed the presence of the metal NPs observed in the TEM images. The XPS spectra (FIGS. 5A-5C) also demonstrated that the metal NPs are localized on the surface of the polymer coating because the Au 4f, Pt 4f, and Pd 3d regions are clearly observable and XPS is most sensitive to the composition in the top few nanometers of the surface. If the metal NPs were embedded inside polymer layers that are 5-29 nm thick then the metal photoelectrons would be completely blocked. The peak shapes and positions of both Au 4f$_{7/2}$ (84 eV) and Pt 4f$_{7/2}$ (71 eV) seem to indicate that most of these atoms are in the Au(0) and Pt(0) state. However, the location and peak shape of Pd 3d$_{5/2}$ indicates that the PdNPs/polymer/ND material is mostly decorated with Pd(II) (337 eV) and that Pd(0) (335 eV) is much less abundant. This difference between the abundance of oxidation states for Au and Pt vs Pd is likely a result of several factors: oxide formation, Pd—S bonding, and incomplete reduction of the precursor Pd salt. TEM images unambiguously confirm the presence of PdNPs, however Pd is also easily oxidized and this oxidation may have contributed to an increase in the relative abundance of Pd(II) vs Pd(0) between the preparation of the PdNPs/polymer/ND material and subsequent XPS analysis. The presence of the polymer on the ND surface was confirmed by S 2p peaks in the XPS spectra (FIG. 5D). The lower intensity of the peaks observed for sulfur compared to that of metal NPs is an indication that the polymer adhesion layer is likely a significantly smaller fraction of the total mass of the composite particles.

Example 6

Scanning Transmission Electron Microscopy (S/TEM)

A JEOL 2800 S/TEM operating at an accelerating potential of 200 kV with a hot field emission gun (FEG) source and equipped with an ultrafast energy dispersive spectrometer was used to collect secondary electron as well as bright and high angular annular dark field (HAADF) images with a probe size of 1.5 nm and a camera length corresponding to a detector semi-angle of 62.1 milliradians. The dual 100 mm$^2$ EDS detectors have a combined solid angle collection efficiency of 1.9 steradians.

Figure 6A:
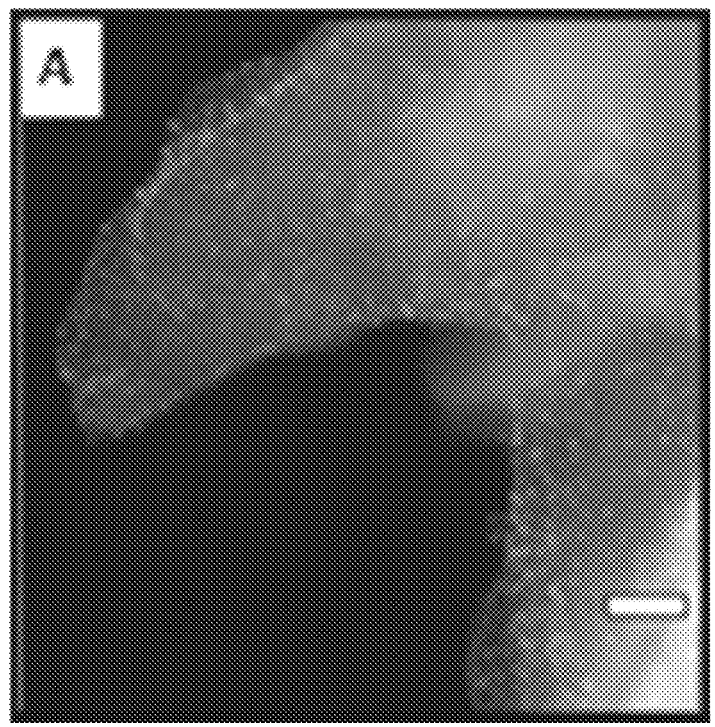
FIG. 6A is an HAADF-S/TEM image of polymer/NDs decorated with Au, in accordance with an example of the present disclosure. Scale bars are 50 nm.
Figure 6B:
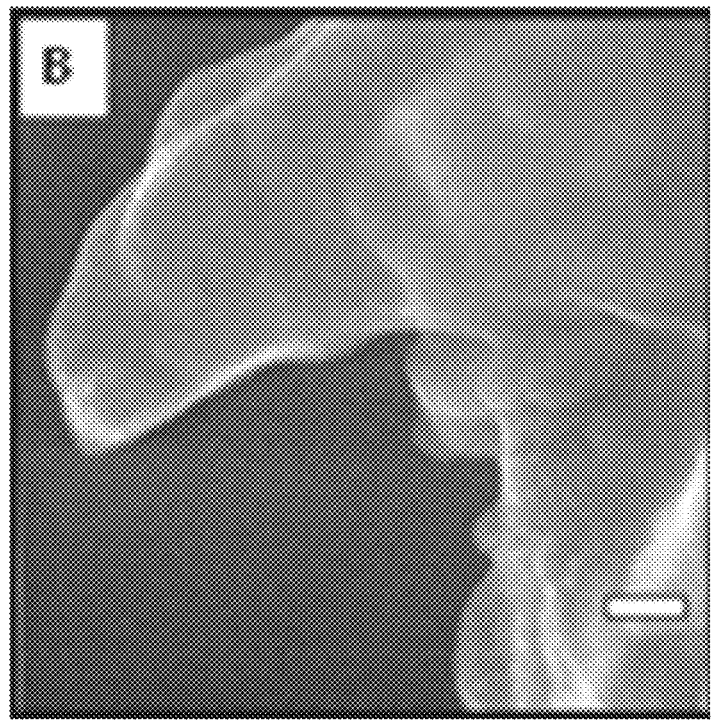
FIG. 6B is an SEI-S/TEM image of the same region as the HAADF-S/TEM image illustrated in FIG. 6A. Scale bars are 50 nm.
Figure 6C:
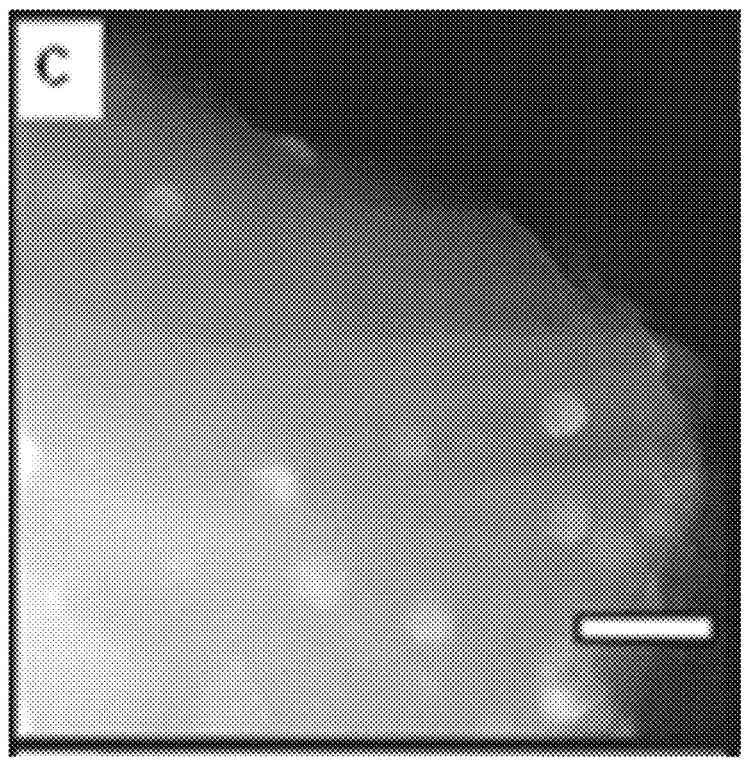
FIG. 6C is an HAADF-S/TEM image of polymer/NDs decorated with Pt, in accordance with an example of the present disclosure. Scale bars are 50 nm.
Figure 6D:
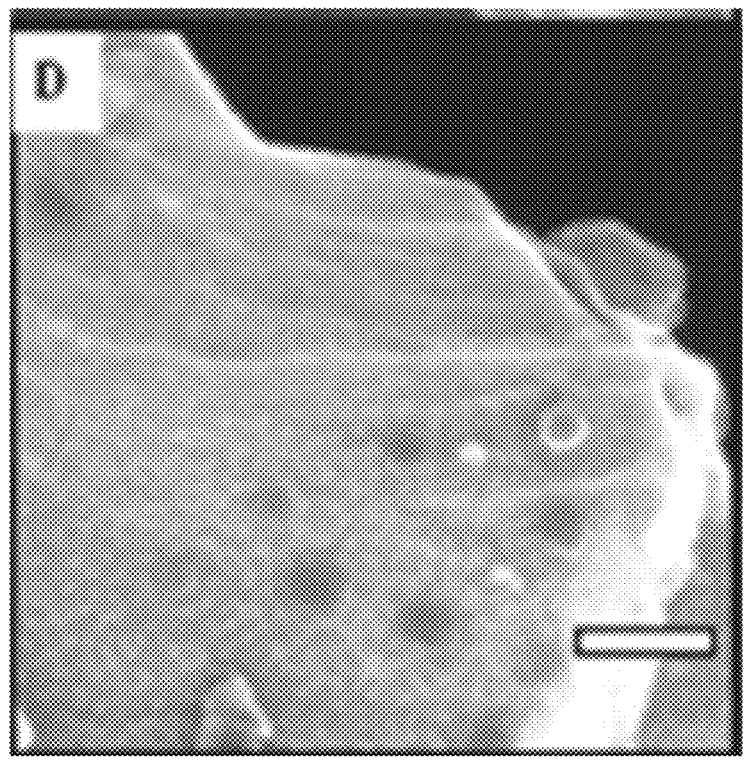
FIG. 6D is an SEI-S/TEM image of the same region as the HAADF-S/TEM image illustrated in FIG. 6C. Scale bars are 50 nm.
Figure 6E:
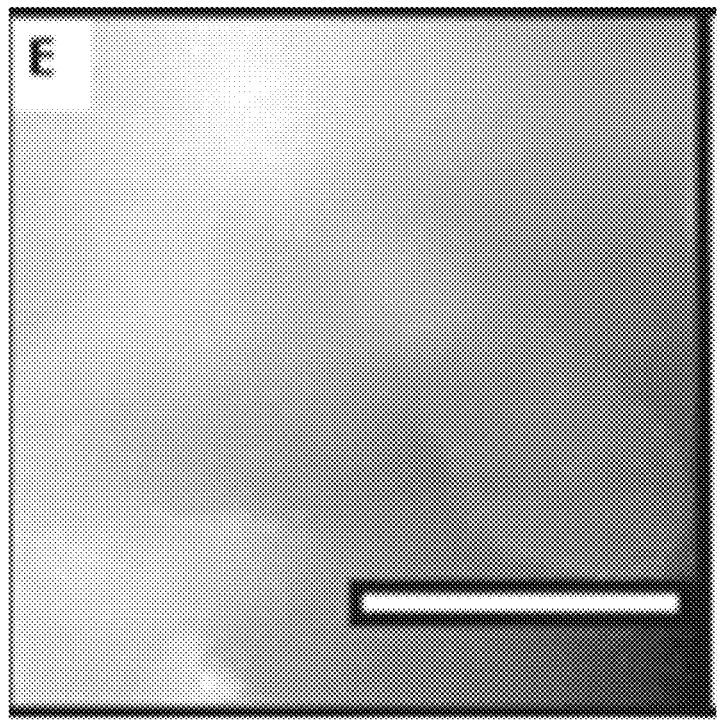
FIG. 6E is an HAADF-S/TEM image of polymer/NDs decorated with Pd, in accordance with an example of the present disclosure. Scale bars are 50 nm.
Figure 6F:
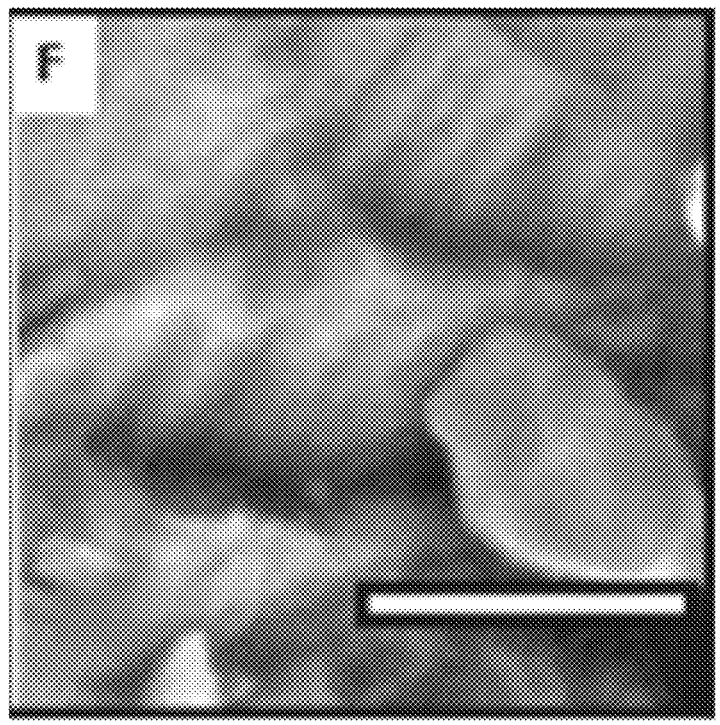
FIG. 6F is an SEI-S/TEM image of the same region as the HAADF-S/TEM image illustrated in FIG. 6E. Scale bars are 50 nm.

High-angle annular dark field-S/TEM (HAADF) was used to study the distribution of the metal NPs on the surface of the composite material (FIGS. 6A, 6C, 6E). HAADF images are formed using high-angle incoherent Rutherford scattered electrons. As the number of protons (Z-number) increases, the scattering cross-sections increase as Z$^2$. As a result, the HAADF technique is particularly suitable for obtaining images of NP/polymer/ND particles. Indeed, Au, Pt and Pd atoms appear nearly 173×, 169×, 58× brighter than carbon atoms in the polymer or diamond support, respectively. Although FIG. 6 reveals that 4.5±0.8 nm (N=101) AuNPs are more easily discernable than the dimmer 1.2±0.3 nm (N=40) PtNPs or the 1.5±0.2 nm (N=62) PdNPs, this difference in contrast most likely results from the significant difference in cluster size. The larger AuNPs contain approximately 2,600 atoms while average PtNPs and the PdNPs are estimated to contain only ~60 and ~100 atoms, respectively. Another interesting observation is that PtNPs not only coated the surface of the polymer/diamond surface as individual clusters, but also as larger loosely packed agglomerates of 18±3 nm (N=14).

Secondary-electron imaging (SEI)-S/TEM images (FIGS. 6B, 6D, 6F) provide clear evidence of the accessibility of the surface-bound noble metal NPs for catalysis. These images offer depth of field at extremely high spatial resolution and show that the metal NPs are not embedded in the polymers, but instead adhered to the surface of the polymer/ND composite particles.

Figure 7A:
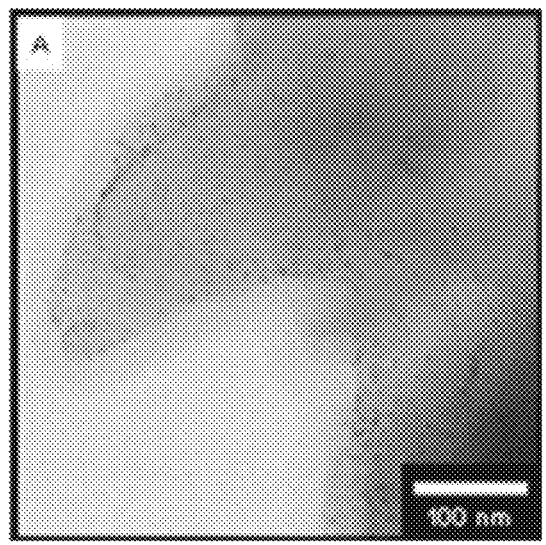
FIG. 7A is a BF-S/TEM image of polymer/NDs decorated with Au, in accordance with an example of the present disclosure.
Figure 7B:
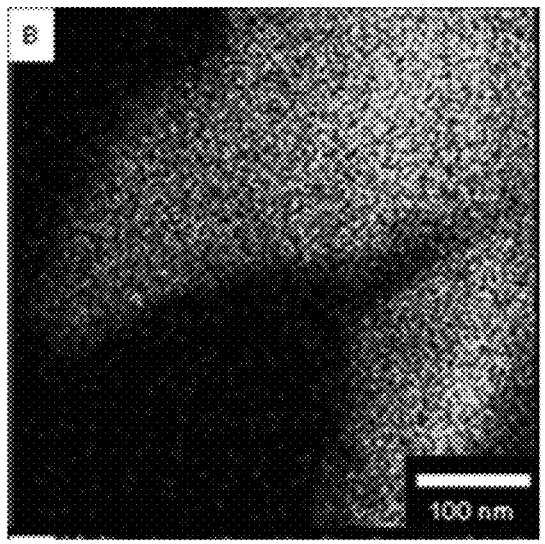
FIG. 7B is an EDS image extracted from the sulfur K-line of the same polymer/NDs depicted in FIG. 7A.
Figure 7C:
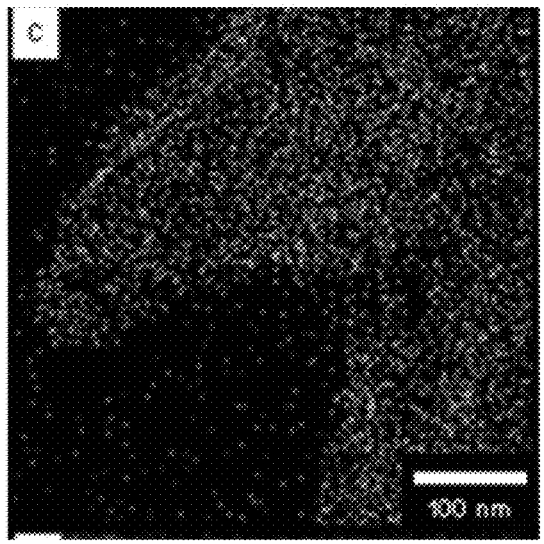
FIG. 7C is an EDS image extracted from the Au M-line of the NP decorated polymer/NDs depicted in FIG. 7A.
Figure 7D:
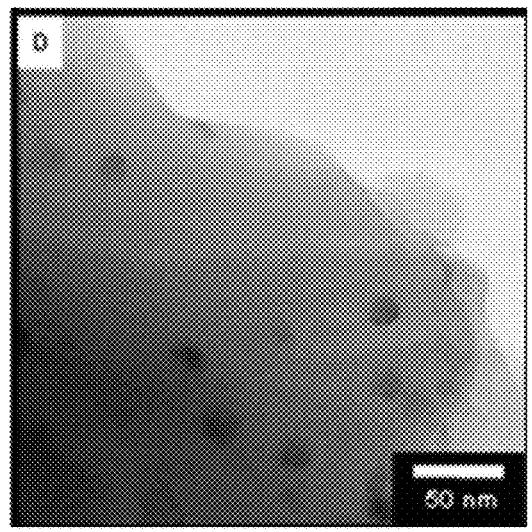
FIG. 7D is a BF-S/TEM image of polymer/NDs decorated with Pt, in accordance with an example of the present disclosure.
Figure 7E:
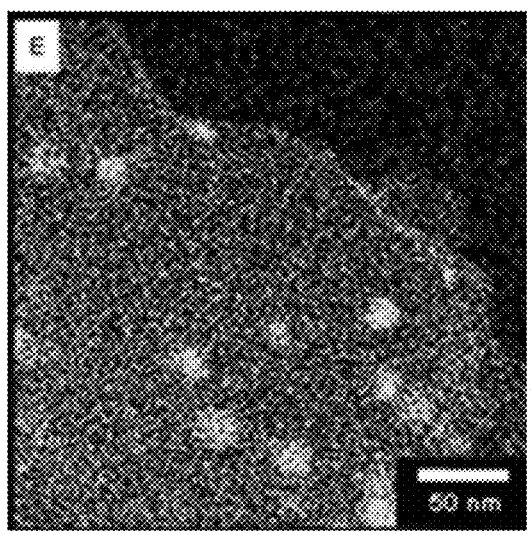
FIG. 7E is an EDS image extracted from the sulfur K-line of the same polymer/NDs depicted in FIG. 7D.
Figure 7F:
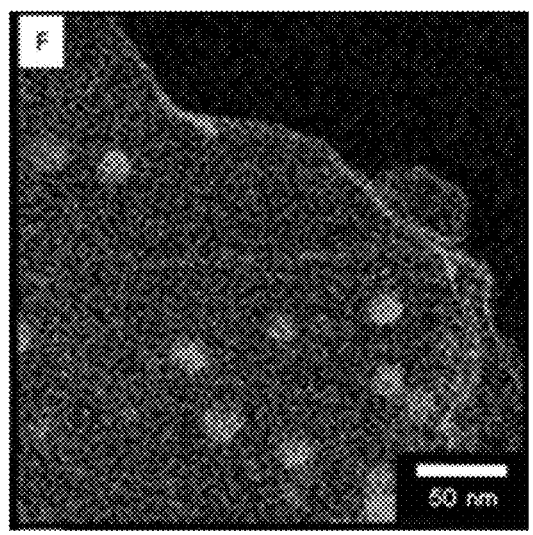
FIG. 7F is an EDS image extracted from the Pt M-line of the NP decorated polymer/NDs depicted in FIG. 7D.
Figure 7G:
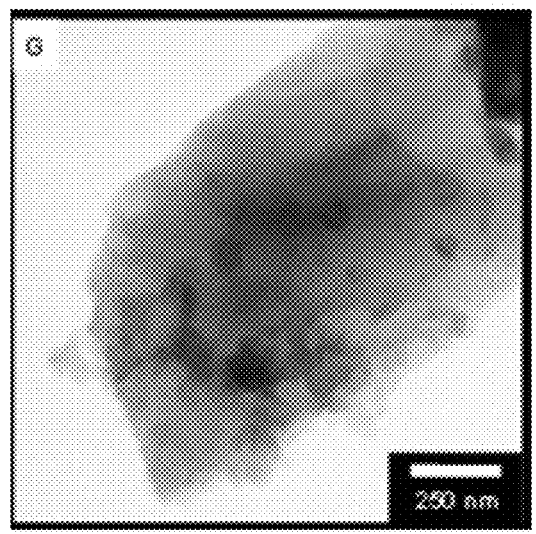
FIG. 7G is a BF-S/TEM image of polymer/NDs decorated with Pd, in accordance with an example of the present disclosure.
Figure 7H:
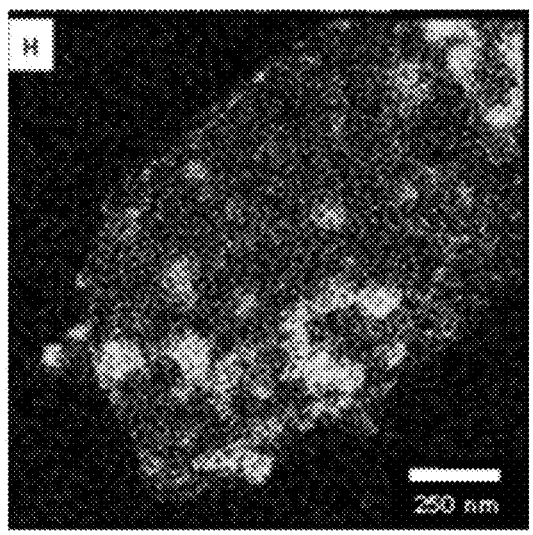
FIG. 7H is an EDS image extracted from the sulfur K-line of the same polymer/NDs depicted in FIG. 7G.
Figure 7I:
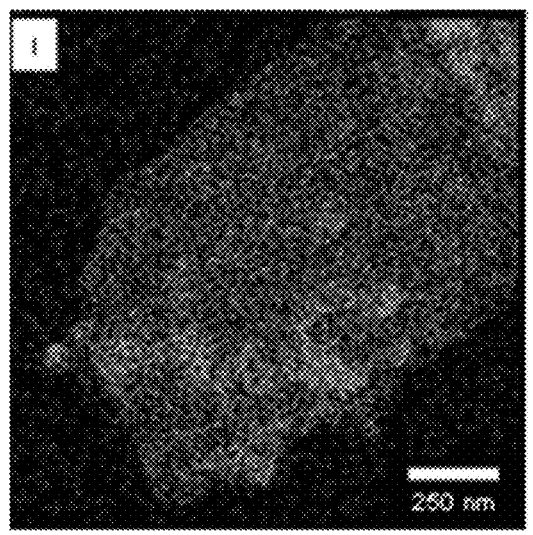
FIG. 7I is an EDS image extracted from the Pd L-line of the NP decorated polymer/NDs depicted in FIG. 7G.
Figure 8A:
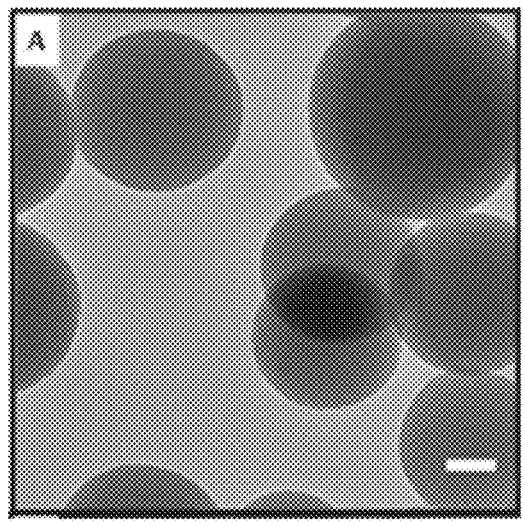
FIG. 8A is a TEM image of AuNP decorated silica spheres, in accordance with an example of the present disclosure. Scale bars are 50 nm.
Figure 8B:
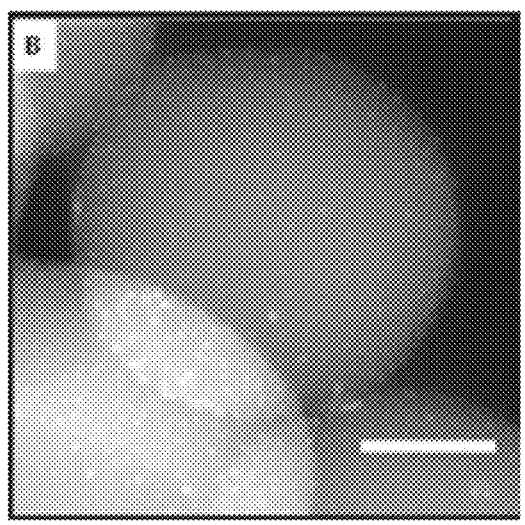
FIG. 8B is a higher magnification HAADF-S/TEM image of the AuNP decorated silica spheres of FIG. 8A. Scale bars are 50 nm.
Figure 8C:
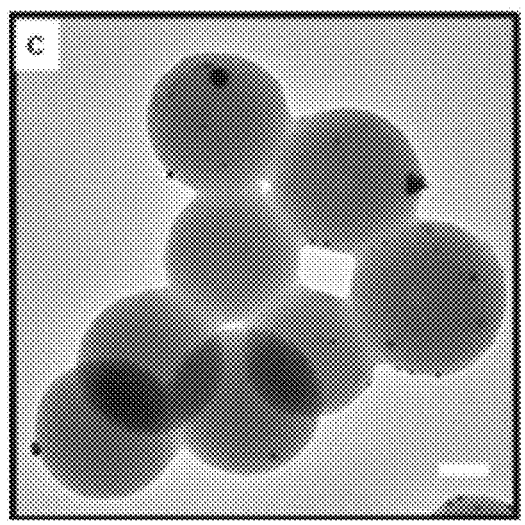
FIG. 8C is a TEM image of the same silica spheres depicted in FIG. 8A after one day of storage in a solution saturated with PNP and $NaBH_4$ (pH of ~14). Scale bars are 50 nm.
Figure 8D:
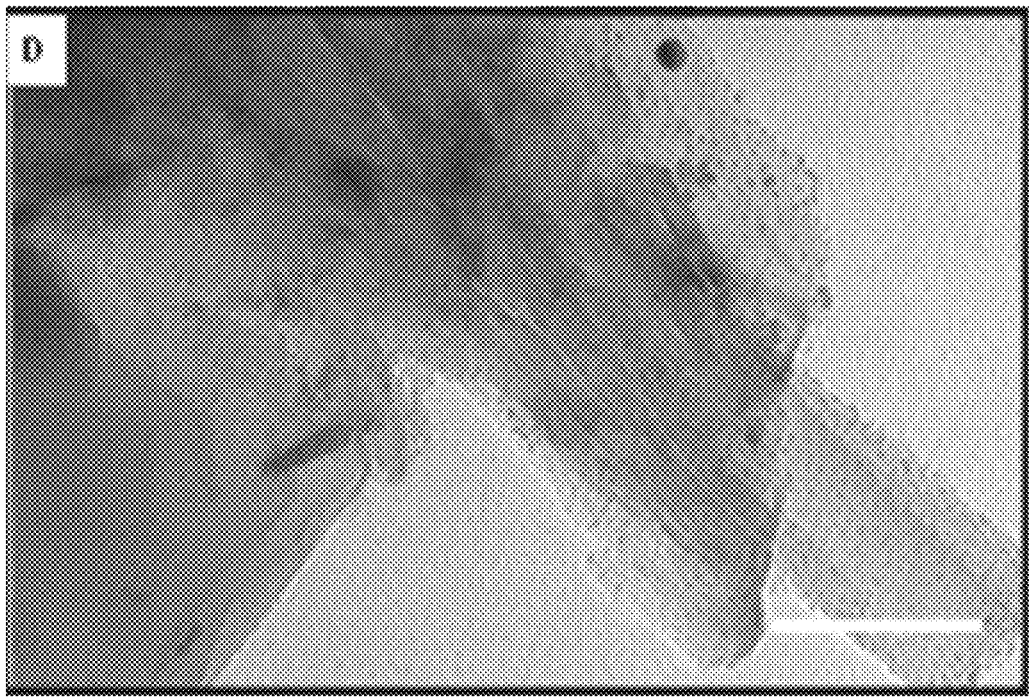
FIG. 8D is a TEM image of bare ND decorated with AuNPs before one week or storage in a solution saturated with PNP and $NaBH_4$ (pH of ~14). Scale bars are 50 nm.
Figure 8E:
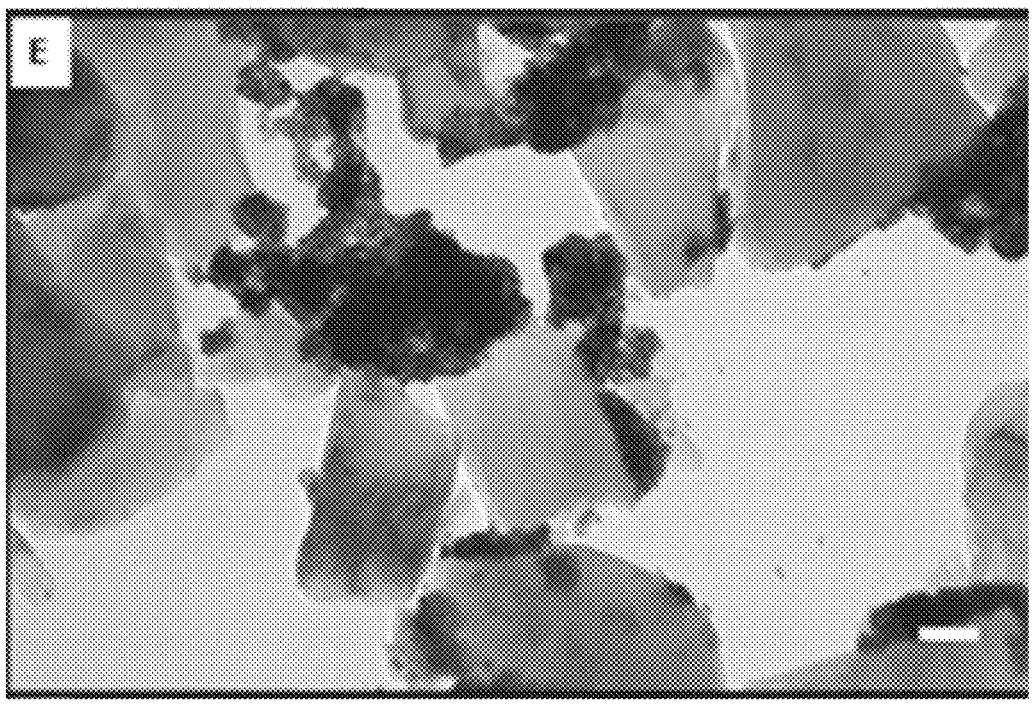
FIG. 8E is a TEM image of bare ND decorated with AuNPs after one week of storage in the saturated solution of PNP and $NaBH_4$ (pH of ~14). Scale bars are 50 nm.
Figure 8F:
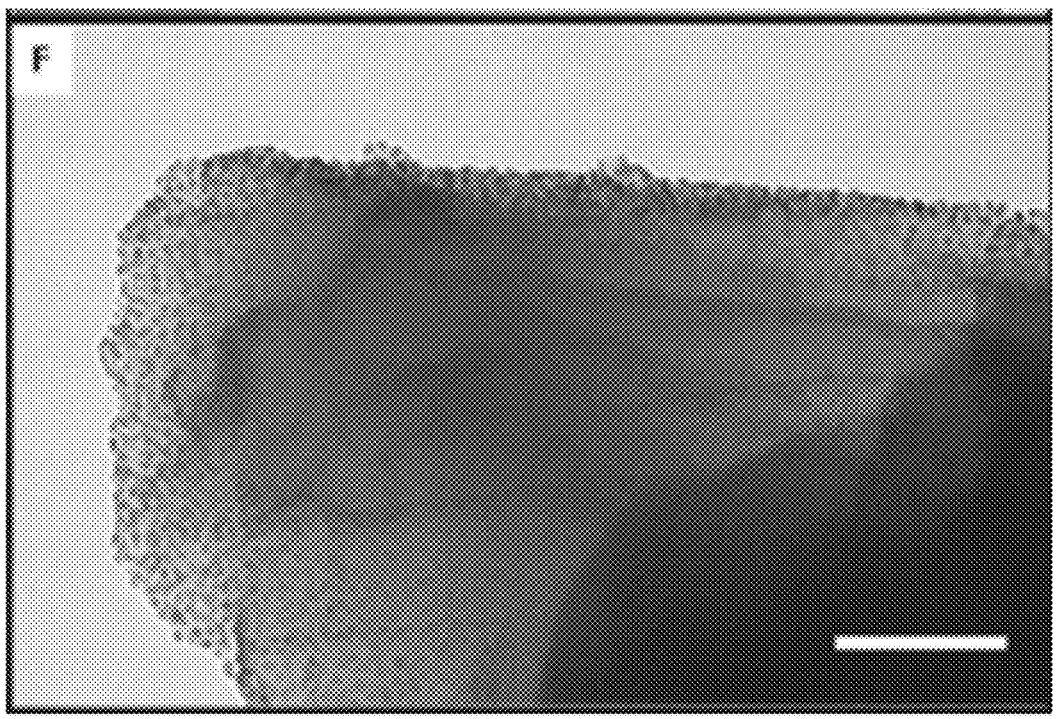
FIG. 8F is a TEM image of AuNP/polymer/NDs before one week or storage in a solution saturated with PNP and $NaBH_4$ (pH of ~14). Scale bars are 50 nm.
Figure 8G:
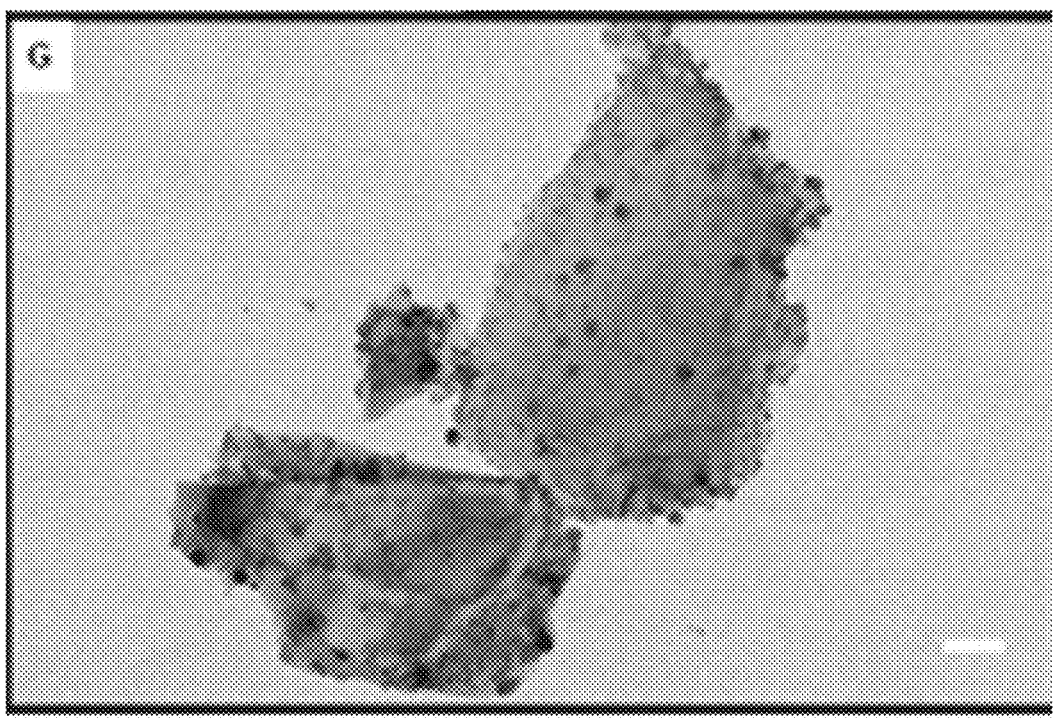
FIG. 8G is a TEM image of AuNP/polymer/NDs after one week of storage in the saturated solution of PNP and $NaBH_4$(pH of ~14). Scale bars are 50 nm.

High resolution energy dispersive spectroscopy (EDS) obtained with S/TEM provided chemical mapping of the polymer and Au, Pt, or Pd NPs attached to the polymer/ND surface. As evident from FIG. 7, the polymer coating appears to cover the entire ND surface. The BF-S/TEM images in FIGS. 7A, 7D, and 7G are clearly correlated to the maps of the characteristic sulfur-K X-rays at 2.3 keV shown in FIGS. 7B, 7E, and 7H. One of the monomers in the polymer coating is PETMP which is a tetra-thiol molecule, the only sulfur-containing molecule. Therefore, the sulfur EDS map indicates that the polymer coating is confined to the surface of the ND shown in the bright field (BF)-S/TEM images. FIGS. 7C, 7F, and 7I correspond to the Au-L, Pt-M, and Pd-L X-ray lines at 9.7, 2.0, and 2.8 keV, respectively. These EDS maps demonstrate that metal NPs are adhered to the surface of the thiol-ene polymer which coats the entire surface of the ND and follows the topography of the diamond surface with high fidelity. These maps complement the XPS data and show that the sulfur bonding environment corresponds to the local attachment of the metal NPs.

Example 7

Catalytic Efficiencies of Catalytic Nanoparticles

Using a Perkin-Elmer Lambda 9 UV/Vis/NIR spectrophotometer, absorbance measurements at 400 nm were collected in time scan mode at intervals of 0.2 s and a bandwidth of 4 nm.

A Thermo Scientific iCAP 6000 series ICP Spectrometer was used for elemental analysis. Samples were digested with freshly prepared hot aqua regia using concentrated Trace-SELECT° $HNO_3$ and HCl obtained from Sigma-Aldrich. Standard solutions were prepared using 1000 ppm metal standards obtained from Inorganic Ventures.

When testing the catalytic efficiencies, $6.54 \times 10^{-5}$, $6.82 \times 10^{-5}$, $6.89 \times 10^{-5}$ g of the Au, Pd, or Pt/polymer/ND materials were used where the mass % metals content was 23.7, 0.75, and 1.14%, respectively. These materials were combined with water so that the final concentrations of the aqueous mixtures were 3 μM 4-NP and 3 mM $NaBH_4$ (at least 1000× molar excess of $NaBH_4$).

Thus, the catalytic properties of NP/polymer/ND composite particles were studied in an aqueous reaction of high significance. The catalytic efficiencies of the Au, Pt, and Pd NPs supported on the polymer/ND particles were probed using the reduction of para-nitrophenol (PNP) to para-aminophenol (PAP) with $NaBH_4$ which is easily followed using UV-Vis absorbance measurements. In addition to the convenient monitoring, this reaction is important because PAP is widely used as a precursor in the industrial synthesis of paracetamol (acetaminophen). Nitrophenols have also been identified as priority pollutants making their conversion to less toxic aminophenols a desirable environmental goal.

Without a catalyst, an aqueous mixture of PNP and $NaBH_4$ persists indefinitely as a clear, bright yellow solution with an absorbance at 400 nm. Upon the addition of the NP/polymer/NDs the PNP absorption band at 400 nm gradually decreases, while a weaker absorption band at 300 nm, corresponding to the reduction product, 4-aminophenol, appears in the UV spectrum. The resulting solution is very basic (8<pH<14), creating a particularly challenging environment for the NP catalysts.

Instead of reporting turnover frequencies (TOFs), we quantify the catalytic activity in units of catalytic cycles per active site per second, a quantity known as the site time yield (STY), $$STY = \frac{5n_p}{6D_M n_m t} \quad [2]$$

where $n_p$ is the number of moles of product produced during the measurement time, $D_M$ is the metal size dispersion, $n_m$ is the total moles of metal atoms used, and t is the measurement time. The ratio of surface atoms to total atoms in a metal cluster is the metal size dispersion, $$D_M = \frac{6n_s M_w}{\rho N d_p} \quad [3]$$

where $n_s$ is equal to the number of metal atoms on the particle surface per unit area, $M_w$ is the molecular weight of the metal, p is the bulk metal density, N is Avagadro's number, and $d_p$ is the diameter of the metal clusters as determined by TEM. The STY calculation takes into consideration the surface area in addition to the total amount of metal to account for the surface specificity of most catalytic processes. In evaluating catalytic efficiencies using STYs, the importance of NP size is accounted for by using $D_M$. This size-related factor takes into account the fact that as the NP diameter decreases, the effective total surface area increases, leading to a greater number of defect sites important to catalysis.

When used as the catalyst for the reduction of PNP, the STYs for Au, Pt and Pd NPs immobilized on polymer/NDs were observed to be within a typical range of reported values for Au and Pd NPs, with AuNPs being less catalytically active than Pd (See Table 1). However, the activity of our PtNPs is higher than expected relative to the Au and Pd NPs. It is possible that the attachment of the PtNPs to the polymer may influence the adsorption energy of PNP leading to a more favorable reaction environment than that of unsupported PtNPs. Comparison of the STYs of the Au, Pd, and Pt NPs on the composite supports observed in this work with those reported for other metal NP systems is very informative. The higher catalytic rates of CTAB-stabilized AuNP materials and other unsupported systems are expected because substrate access to active sites is unhindered whereas supported NPs are much less accessible. However, while possessing these extremely high activities, unsupported NPs are highly susceptible to aggregation and subsequent loss of catalytic activity. As a comparison, STYs for PNP reduction for catalyst NPs supported on $SiO_2$ and $TiO_2$ are also presented in Table 1. In these examples, $SiO_2$ supported NPs exhibit higher rates of PNP conversion, however, these studies neglected to show, as we have, that $SiO_2$ readily dissolves in this high pH reaction solution. This instability of $SiO_2$-based supports is the most compelling reason not to use these materials for acidic/basic aqueous reactions. Although the polymer/ND composites presented in this study exhibit lower conversion rates, their stability surpasses that of $SiO_2$ based systems as shown below.

TABLE 1

Comparison of catalytic efficiencies of catalytic nanoparticles described herein and other comparative materials.

| Metal NP/ support | Rate constant $(s^{-1})^a$ | STYs $(s^{-1})^b$ | T (K) | NP Size (nm) | PNP/$NaBH_4$/ metal NP (mol/mol/mol) |
|---|---|---|---|---|---|
| Polymer/ND | — | — | 298 | — | 1/1000/— |
| Au/polymer/ND | — | $3.0\ (\pm 1.0) \times 10^{-3}$ | 298 | 4.5 ± 0.8 | 0.076/76/1 |
| Au/$SiO_2$<sup>c</sup> | $3.24 \times 10^{-1}$ | 8 | 298 | 10 | 10/1000/1 |
| Au/$TiO_2$<sup>d</sup> | $3.01 \times 10^{-11}$ | $4.0 \times 10^{-2}$ | 298 | 19 | 8/2814/1 |

TABLE 1-continued

Comparison of catalytic efficiencies of catalytic nanoparticles described herein and other comparative materials.

| Metal NP/<br>support | Rate<br>constant<br>$(s^{-1})^a$ | STYs<br>$(s^{-1})^b$ | T<br>(K) | NP Size<br>(nm) | PNP/NaBH$_4$/<br>metal NP<br>(mol/mol/mol) |
|---|---|---|---|---|---|
| Pt/polymer/ND | — | 2.1 (±0.3) × 10$^{-2}$ | 298 | 1.2 ± 0.3 | 1.49/1490/1 |
| Pt/SiO$_2$ | 1.40 × 10$^{-1}$ | 3 | 298 | 8 | 10/1000/1 |
| Pt/TiO$_2$$^d$ | 1.79 × 10$^{-11}$ | 6.4 × 10$^{-3}$ | 298 | 5 | 8/2787/1 |
| Pd/polymer/ND | — | 1.8 (±0.4) × 10$^{-2}$ | 298 | 1.5 ± 0.2 | 1.25/1250/1 |
| Pd/SiO$_2$ | 7.15 × 10$^{-1}$ | 37 | 298 | 20 | 10/1000/1 |
| Pd/TiO$_2$$^d$ | 3.29 × 10$^{-11}$ | 6.4 × 10$^{-3}$ | 298 | 5 | 5/1520/1 |

$^a$Observed rate constant
$^b$STY normalized using equations [2] and [3]
$^c$SBA-15 mesoporous silica
$^d$Reported TOF values used to calculate rate constant and STY Example 8

Catalytic Nanoparticle Stability

Synthesis of TPP-AuNPs: In a mixture of acetonitrile and toluene (10:40 mL), 0.017 g (0.05 mmol) of chloro(triethylphosphine)gold(I) (Et$_3$PAuCl) was dissolved. TPP (0.0786 g, 0.3 mmol) was added to the mixture at room temperature. The contents were stirred for 30 min after which 0.4 mL of 9-BBN (0.2 mmol) was injected into the mixture. After an additional 30 min of stirring, a solid appeared. The reaction mixture was centrifuged and the solid was collected. The solid then was washed twice with hexane to remove any impurities. After drying by nitrogen flow, a black solid was obtained. The black solid obtained above was dissolved in nanopure water, (>18 MQ) and the mixture sonicated in a Branson ultrasonic cleaner. The solution was centrifuged and the small aggregates at the bottom of the tube were discarded. The supernatant was centrifuged two more times and the final solution was used as the stock TPP AuNP solution in the following catalysis investigations.

Preparation of Silica Supported AuNPs: Roughly 1.2 g of 250 nm silica spheres, produced according to the Stöber method, were treated with fresh 100° C. piranha solution overnight. The silica was then washed with copious amounts of water and ACN, then dried with nitrogen. The cleaned and dried silica was added to a solution of 40 mL ACN, to which ~1 mL of MCPTMS was added. The mixture was stirred for 48 hours after which the silica was washed with copious amounts of ACN. The MCPTMS coated silica was then added to 5 mL of TPP stabilized AuNPs (2.4 µM Au in H$_2$O) and the solution was stirred for 24 hours and then rinsed thoroughly with ACN.

Preparation of Bare Diamond Supported AuNPs: 2.2 g of 0.25 µm MDP diamond solution (6.21% in H$_2$O) was added to 4.9 g of Au/ACN mix (0.071 molal Et$_3$PAuCl in ACN) and stirred for at least 30 minutes, after which a five-fold mol excess (with respect to moles of Au salt) of NaBH$_4$ in 5 mL H$_2$O was added dropwise and allowed to continue mixing for 30 minutes before rinsing with ACN and H$_2$O and then drying with nitrogen.

The stability of the AuNP/polymer/ND particles in an aqueous environment of high pH was compared to two known supported catalysts: AuNPs on mercaptosilane-coated silica spheres and AuNPs on bare diamond. AuNP/polymer/NDs and AuNP/NDs were stored for one week in an aqueous solution saturated with 4-NP and NaBH$_4$ (with pH of ~14). In the case of the AuNP/mercaptosilane/SiO$_2$ materials, the particles were only exposed for one day to avoid complete dissolution. As seen in FIG. 8, the AuNPs on silica spheres and bare ND formed large aggregates. As expected, the silica spheres also dissolved in the extremely basic solution. Although the AuNPs on the polymer/ND samples did begin to aggregate, the extent of the aggregation was significantly smaller than that for the AuNPs supported on silica particles or AuNPs on bare NDs. When stored dry at ambient conditions for >6 months, the AuNPs on bare diamond aggregated extensively, whereas the AuNP/polymer/NDs showed no noticeable aggregation.

The stability of the polymer/ND particles was also tested with a variety of polar and nonpolar organic solvents. The composites remained unchanged after rinsing with copious amounts of acetone, isopropanol, acetonitrile, hexanes, methylene chloride, chloroform, and toluene. This is a critical advantage over polymer-only supports, such as polystyrene, which swell and dissolve in most organic solvents. Thus, NP coated polymer/ND particles are significantly more robust than silica, diamond, or polymer particles alone.

Example 9

Fluorescent Tagging and Imaging

Rhodamine B and dansyl chloride were attached to the same AuNP/polymer/ND materials described above using known methods. Fluorimetry spectra were acquired using a Hitachi F-7000 Fluorescence Spectrophotometer. Fluorescence images were collected using an Olympus BX40 fluorescence microscope with a Photometrics CoolSNAPcf color camera made by Roper scientific. The excitation/emission filter set was 557/571 nm and the acquisition time was 0.01 s.

Figure 9A:
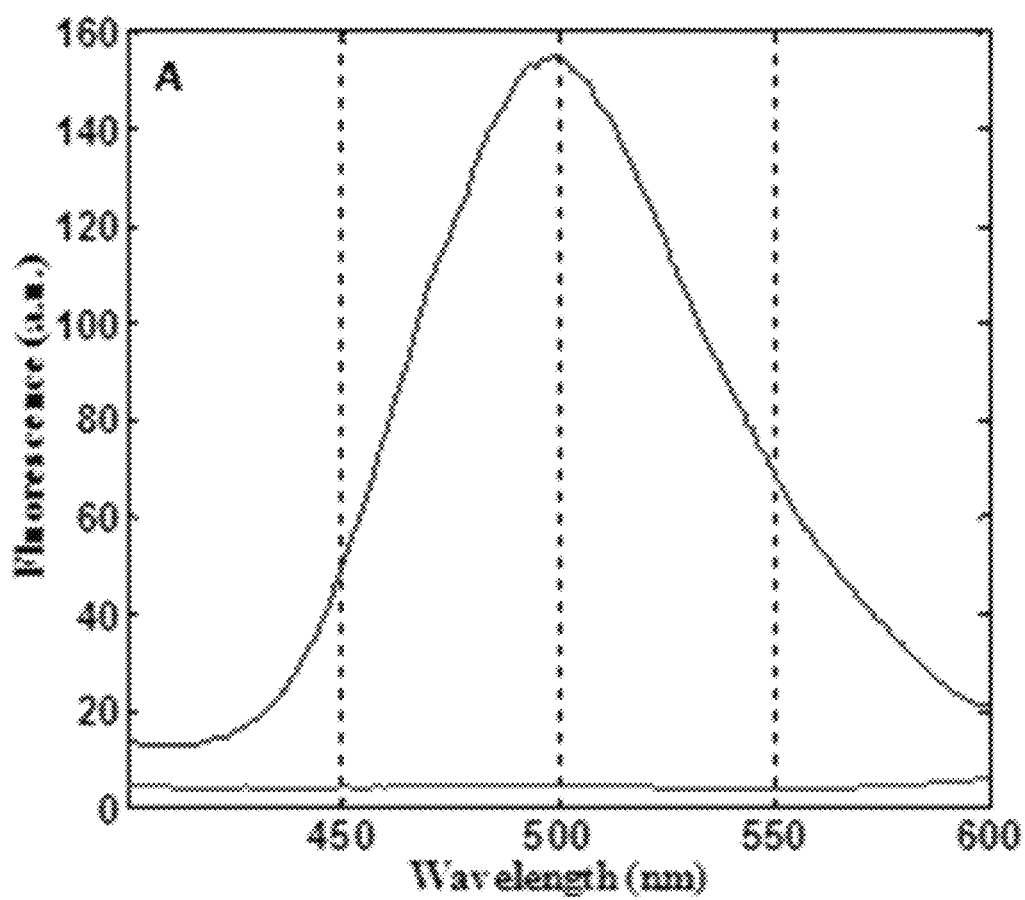
FIG. 9A is a fluorescence spectrum of bare ND (bottom) and after the treatment with dansyl chloride (top).
Figure 9B:
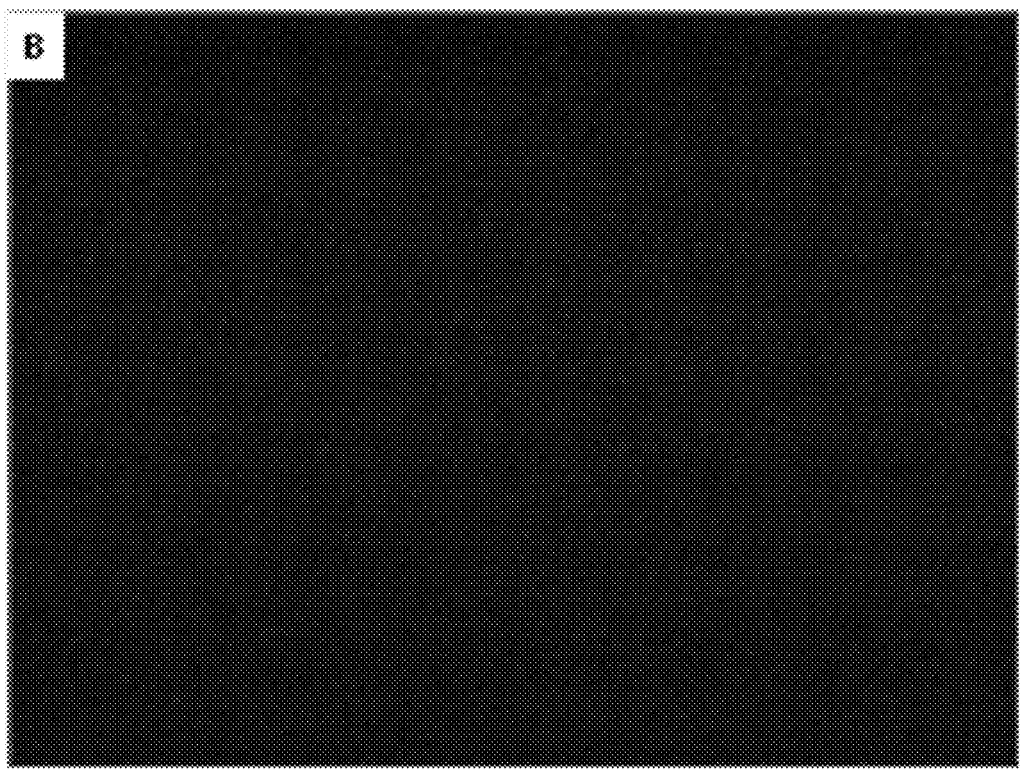
FIG. 9B is an epifluorescence microscopy image of 1.0 µm bare diamond treated with rhodamine B.
Figure 9C:
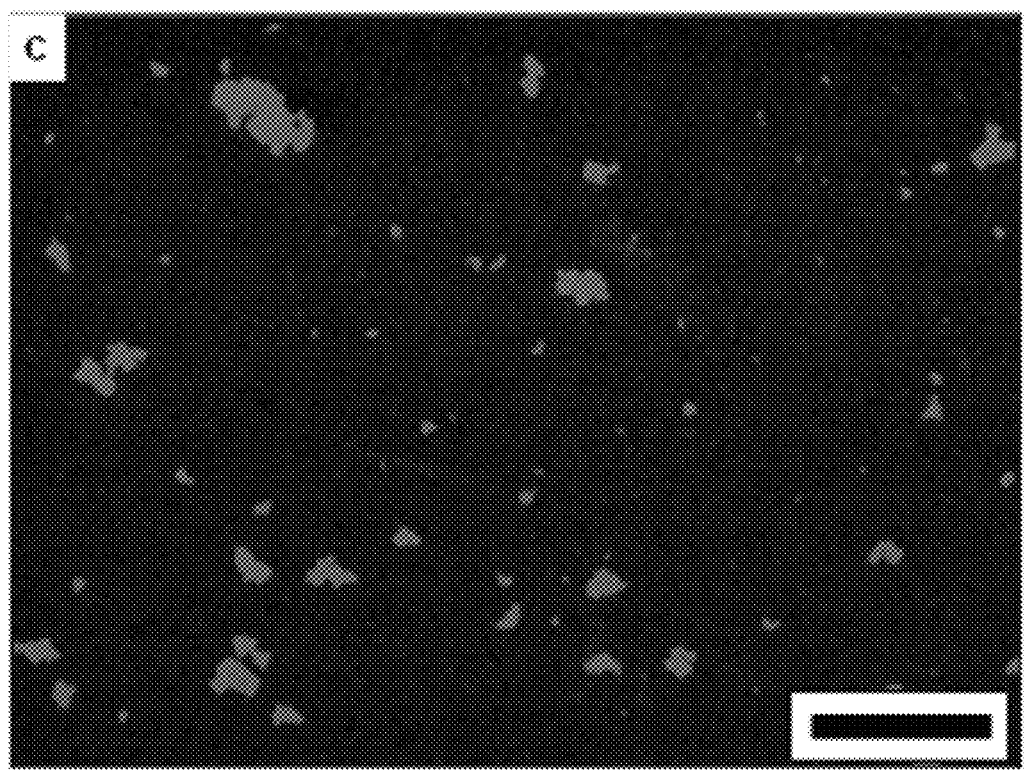
FIG. 9C is an epifluorescence microscopy image of polymer/ND composites treated with rhodamine B. Scale bar is 10 µm.

Traditional methods for surface modification of diamond require the use of high temperatures and pressures and of potentially harmful chemicals. The method of coating nanodiamond with a polymer described herein creates a surface with numerous post-functionalization possibilities. To probe the ability to surface immobilize small molecules, the reactivity the primary amine groups in the polymer was investigated by attaching fluorescent tags. The incorporation of primary amine groups was accomplished by doping the monomer mixtures, which contained the metal salts and were identical to the materials prepared to support the NP catalysts, with either AMPAA or AEMA, two methacrylate monomers containing primary amines. Polymer/NDs were treated with dansyl chloride and rhodamine B, which react with primary amines to form covalent bonds, and measured the fluorescence of the resulting materials (FIG. 9). Fluorimetry data showed strong fluorescence of dansylated polymer/NDs at 500 nm with an excitation wavelength of 300 nm indicating that dansyl chloride had indeed attached to the primary amines of the polymer coating. Separately, epifluorescence microscopy showed negligible background fluorescence for bare nanodiamond, while polymer/NDs exhibited strong fluorescence when treated with rhodamine B (FIGS. 9B and 9C). Thus, both of these fluorescent tags were successfully attached to the AuNP/polymer/ND surface, confirming the presence, accessibility and reactivity of the primary amine groups.

Example 9

Radical initiated polymerization was used to modify the surface of diamond to allow compatibility and adhesion for metallic nanoparticles or other catalytic materials. The material is prepared by mixing monomer molecules with diamond (sizes may range 0.001-2 um). After mixing thoroughly, the mixture continues stirring while being exposed to a UV lamp (254 nm radical production by cleavage of DMPA). After exposure and subsequent mixing the solids are rinsed with copious solvents. The solids are then mixed with acetonitrile, water, and a metallic salt. After thorough mixing, an aqueous sodium borohydride solution is added dropwise up to a 5-fold molar excess (compared to the moles of metal). The amount of sodium borohydride added controls metallic nanoparticle size and surface density. More sodium borohydride leads to denser packing and eventually larger metallic nanoparticles. The solids are then rinsed in copious amounts of water and solvents to remove any unreacted reagents. The solids are stored in ethanol or dried with nitrogen. Catalytic activity of the composite material was confirmed with the model reaction: 4-nitrophenol reduces to 4-aminophenol in the presence of excess sodium borohydride followed by UV-Vis spectrophotometry.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A catalytic nanoparticle, comprising:
   a nanodiamond core;
   a thin-layer polymeric film applied to an outer surface of the nanodiamond core; and
   a catalyst immobilized at an outer surface of the thin-layer polymeric film.
2. The catalytic nanoparticle of claim 1, wherein the nanodiamond core has a size of from about 50 nm to about 500 nm.
3. The catalytic nanoparticle of claim 1, wherein the nanodiamond core is unhydrogenated.
4. The catalytic nanoparticle of claim 1, wherein the thin-layer polymeric film has a thickness of from about 1 nm to about 100 nm.
5. The catalytic nanoparticle of claim 4, wherein the thickness is from 5 nm to 20 nm.
6. The catalytic nanoparticle of claim 1, the thin-layer polymeric film further comprising a polymer having a S—C bond.
7. The catalytic nanoparticle of claim 1, wherein the catalyst is an enzyme.
8. The catalytic nanoparticle of claim 1, wherein the catalyst is a noble metal.
9. The catalytic nanoparticle of claim 8, wherein the noble metal is gold, platinum, palladium, silver, rhodium, osmium, iridium, ruthenium, combinations thereof, or alloys thereof.
10. The catalytic nanoparticle of claim 1, wherein the catalyst is immobilized via bonding with a sulfur atom at the outer surface of the thin-layer polymeric film.
11. A method of catalysis, comprising:
    contacting the catalytic nanoparticle of claim 1 with a reactant in a reaction area, said reactant being capable of forming a reaction product via a reaction catalyzed by the catalyst; and
    facilitating a catalytic interaction between the catalytic nanoparticle and the reactant.
12. The method of claim 11, wherein the catalytic nanoparticle is a heterogeneous catalyst.
13. The method of claim 11, wherein the catalytic nanoparticle is fixed to a porous material.
14. The method of claim 11, wherein the catalytic nanoparticle is a homogeneous catalyst.
15. The method of claim 11, wherein the catalytic nanoparticle is dispersed in a fluid.
16. The method of claim 11, wherein the fluid is a solution.
17. The method of claim 11, wherein the solution has a pH of greater than or equal to 8.
18. The method of claim 11, wherein the solution has a pH of less than or equal to 5.
19. A sensor, comprising:
    a transducer; and
    a catalytic nanoparticle according to claim 1 positioned relative to the transducer to facilitate detection of a target analyte.
20. The sensor of claim 19, wherein the transducer comprises an electrochemical transducer, potentiometric transducer, amperometric transducer, conductometric transducer, chemicapacitive transducer, chemiresistive transducer, photoionizing transducer, physical transducer, optical transducer, a biochemical transducer, an affinity-based transducer, a thermochemical transducer, a piezoelectric transducer, or a combination thereof.
21. The sensor of claim 19, wherein the catalytic nanoparticle forms part of the transducer.
22. The sensor of claim 19, wherein the catalytic nanoparticle is positioned separate from the transducer.
23. The sensor of claim 19, wherein the catalyst comprises an enzyme, a noble metal, or a combination thereof.
24. The sensor of claim 23, wherein the noble metal is a member of the group consisting of gold, silver, and combinations thereof.
25. The sensor of claim 19, further comprising a light source positioned to direct electromagnetic irradiation toward the transducer, the catalytic nanoparticle, or both.

* * * * *